US008067039B2

(12) United States Patent
Wu

(10) Patent No.: US 8,067,039 B2
(45) Date of Patent: Nov. 29, 2011

(54) **EXTRACT OF PLANT *DENDROBII CAULIS* AND PREPARING PROCESS THEREOF**

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 12/316,216

(22) Filed: Dec. 10, 2008

(65) Prior Publication Data

US 2009/0208595 A1 Aug. 20, 2009

Related U.S. Application Data

(60) Continuation of application No. 11/240,183, filed on Sep. 30, 2005, now abandoned, which is a division of application No. 10/648,651, filed on Aug. 25, 2003, now Pat. No. 7,101,577.

(51) Int. Cl.
*A61K 36/78* (2006.01)
(52) U.S. Cl. ........................................ 424/725; 424/779
(58) Field of Classification Search ........................ None
See application file for complete search history.

(56) References Cited

FOREIGN PATENT DOCUMENTS

| CN | 1078148 | A | * | 11/1993 |
| CN | 1108949 | A | * | 9/1995 |
| CN | 1137385 | | * | 12/1996 |
| CN | 1137385 | A | | 12/1996 |

OTHER PUBLICATIONS

Higashide (American Journal of Ophthalmology (2003), vol. 136, No. 3, pp. 567-569).*
http://dictionary.reference.com/browse/caulis—accessed Jun. 2010.*
http://myhealthspan.com/DendrobiumStem.shtm—accessed Jun. 2010.*
English translation of Miao (CN 1137385)—1996.*
Mayerson, P.L. and Hall, M.O., "Rat Retinal Pigment Epithelial Cells Show Specificity of Phagocytosis in Vitro," J. Cell Biol., 103: 299-308, 1986.
Boulton, M. and Marshall, J., "Effects of Increasing Numbers of Phagocytic Inclusions on Human Retinal Pigment Epithelial Cells in Culture: A Model for Aging," British Journal of Ophthalmology,70: 808-815, 1986.
Panda-Jonas, S., Jonas, J.B., and Jakobczyk-Zmija,M., "Retinal Photoreceptor Density Decreases with Age," Ophthalmology, 102:1853-1859, 1995.
Goldstein, I.M., Ostwal, P. and Roth, S., "Nitric Oxide: A Review of Its Role in Retinal Function and Disease," Vision Res., 1996, 36(18): 2979-2994.
Tilton, R.G. et al.,"Prevention of Diabetic Vascular Dysfunction by Guanidines, Inhibition of Nitric Oxide Synthase Versus Advanced Glycation End-Product Formation," Diabetes, 1993, 42(2): 221-232.
Goureau O., Hicks, D. and Courtois, Y., "Human Retinal Pigmented Epithelial Cells Produce Nitric Oxide in Response to Cytokines," Biochem. Biophys Res. Comm., 1994, 198(1): 120-126.

Lu, M., Kuroki, M. et al., "Advanced Glycation End Products Increase Retinal Vascular Endothelial Growth Factor Expression," J. Clin. Invest., 101: 1219-1224, 1998.
Munch, G., Thome, J. et al., "Advanced Glycation Endproducts in Ageing and Alzheimer's Disease," Brain Research Reviews, 23: 134-154, 1997.
Handa, J.T., Verzijl, N. et al., "Increase in the Advanced Glycation End Product Pentosidine in Bruch's Membrane with Age," Investigative Ophthalmology & Visual Science, 40: 775-779, 1999.
Zimmerman, G.A., Meistrell, M. et al., "Neurotoxicity of Advanced Glycation Endproducts During Focal Stroke and Neuroprotective Effects of Aminoguanidine," Proc. Natl. Acad. Sci. USA, 92: 3744-3748, 1995.
Handa, J.T., Resiser, K.M. et al., "The Advanced Glycation Endproduct Pentosidine Induces the Expression of PDGF-B in Human Retinal Pigment Epithelial Cells," Exp. Eye Res., 66: 411-419, 1998.
Li, Q., Weng, J. et al., "Hepatocyte Growth Factor and Hepatocyte Growth Factor Receptor in the Lacrimal Gland, Tears, and Cornea," Ophthalmol Vis. Sci., 37: 727-739, 1996.
"Clear Eye Herbal Tea" website (http://web.archive.org/web/20011221015351/http://herbalremedies.com/hk-22b.html—internet archived version from Dec. 2001).
http://www.nlm.nih.gov/medlineplus/ency/article/001000.htm—accessed Jun. 2008.
Science Bulletin (Jul. 2002), vol. 34, No. 7, National Science Council, R.O.C.
Sun, W., Funakoshi, H. et al., "Differential Expression of Hepatocyte Growth Factor and Its Receptor, c-Met in the Rat Retina During Development," Brain Res., 851:46-53, 1999.
He, P.m., He, S. et al., "Retinal Pigment Epithelial Cells Secrete and Respond to Hepatocyte Growth Factor," Biochem. Biophys. Res. Commun., 249: 253-257, 1998.
Miyazawa, M., Antimutagenic Activity of Gigantol From *Dendrobium nobile*, J. Agric. Food Chem. 1997, 45, pp. 2849-2853.
Clough, J. "Rolf Krebs discusses the pharma industry past, present and future", DDT 7(19):990-991 (2002).
Strayss, O. "The Retinal Pigment Epithelium in Visual Function", Physiol Rev 85:845-881 (2005).
Wenzel et al., "Moledular Mechanisms of light-induced photoreceptor apoptosis and neuroprotection for retinal degeneration", Progress in Retinal and Eye Research 24:275-306 (2005).
Handa et al.,"Increase in the Advanced Glycation End Product Pentosidine in Burch's Membrane with Age", Invest Opthamol Vis Sci 40(3):775-779 (1999).
Sheikpranbabu et al., "Pigment epithelium-derived factor inhibits advanced glycation end-product-induced angiogenesis and stimulates apoptosis in retinal endothelial cells," Life Sciences 85:719-731 (2009).

(Continued)

*Primary Examiner* — Susan Hoffman
(74) *Attorney, Agent, or Firm* — Porzio, Bromberg & Newman, P.C.

(57) ABSTRACT

An extract of plant *Dendrobii Caulis* and preparing process thereof are provided. A physiologically active extract of a plant *Dendrobii Caulis* and the method thereof are provided in the present invention. The extract is obtained by an extraction of the plant or parts thereof with a water miscible organic solvent or a mixture thereof with water.

6 Claims, 33 Drawing Sheets

OTHER PUBLICATIONS

Wenzel et al., "Molecular mechanisms of light-induced photoreceptor apoptosis and neuroprotection for retinal degeneration", Progress in Retinal Cell Research 24:275:306 (2005).

Hiscott et al., Matrix and the Retinal Pigment Epithelium in Proliferative Retinal Disease, Progress in Retinal and Eye Research 18(2):167-190 (1999).

* cited by examiner (A) β-actin (B) bFGF (a) DCM 100 μg/ml (b) DCM 10 μg/ml (c) DCM 1 μg/ml (d) HGF (50 ng/ml)

(e) Control

EXTRACT OF PLANT *DENDROBII CAULIS* AND PREPARING PROCESS THEREOF

CROSS-REFERENCE TO RELATED APPLICATION

This application is a continuation of U.S. patent application Ser. No. 11/240,183, filed Sept. 30, 2005, now abandoned, which is a divisional of U.S. patent application Ser. No. 10/648,651, filed Aug. 25, 2003, now U.S. Pat. No. 7,101,577, the entirety of which is hereby incorporated by reference into this application.

FIELD OF THE INVENTION

This invention relates to a process for preparing an extract from a plant and the extract thereof, and especially to one process of using a water miscible organic solvent or a mixture thereof with water for obtaining an extract from the plant.

BACKGROUND OF THE INVENTION

Nowadays, the *Dendrobium* species is considered to be the most precious Chinese herb for treating ophthalmic defects. A *Dendrobium* species belongs to an orchid family, and its steam is the mainly medicinal part. It tastes a little sweet and brackish. Some Chinese medical codices disclose that the *Dendrobium* species is the curative for some illnesses such as salivary defects, stomach defects, and ophthalmic defects. According to our previous research experience, it appears that the *Dendrobii Caulis* is the most medicinal species.

A retinal pigment epithelium (RPE) is a monolayer cell at the surface layer of the retina, which is located between the Bruch's membrane and the photoreceptors. The villous processes at the top of RPE are connected to the outer segments of the photoreceptors, and the basal infloldings at the bottom of RPE are connected to the choroids via the Bruch' membrane. Since the RPE can effectively remove or transmit the toxic materials and the metabolite of the choroid coat and the retina, it performs a very important blood-retinal barrier. In addition, the RPE has many functions, such as receiving light, phagocytizing the outer segments separated from the rod cell and the cone cell because of light stimulation, catabolizing the phagosome, synthesizing the extracellular matrix and the melanin, detoxifying the medicine, providing the essential material for reproducing the outer segments of the photoreceptor, storing and transmitting the Vitamin A, synthesizing the rhodospin, and forming the adherent force of the retina. According to the statistics, a RPE of rat can remove 25000 outer segments separated from the rod cells and the cone cells because of light stimulation in one day, which obviously shows the importance of the frequent phagocytic metabolism (Mayerson and Hall, 1986). The normal phagocytosis of the RPE plays a critical role in maintaining the health of the photoreceptors in the retina. Once the function of phagocytosis is reduced, it will result in the degeneration of the photoreceptors. Although the RPE will be dead or moved to someplace else with the increasing age, the aged RPE still owns the phagocytic ability. However, the digestion ability of the RPE is obviously reduced (Boulton and Marshall, 1986). It appears that the numbers of the human photoreceptors will be decreased per year with a rate ranged from 0.2 to 0.4% per year (Panda-Jonas et al., 1995). Further, the lost quantity of the rod cells are more than those of the cone cells, which causes the diseases and the vision degradation of the aged people. Therefore, maintaining the RPE function is quite important for the visional system.

Although a nitric oxide (NO) is a small, unstable gas molecule with a half-life of several seconds, it has various kinds of physiological functions. Since the NO is an electrically neutral gas, it can arbitrarily penetrate the cell wall. On the other hand, since the NO has the unpaired electron, the NO molecule is highly reactive as the free radicals so that it will penetrate the cell membrane and react immediately after being formed. In the immune system, the NO plays a defensive role and is toxic to cells. In the blood vessel system, the NO is a so-called endothelium derived relaxing factor (EDRF). And, in the central nervous system, the NO acts as a neurotransmitter.

The NO is released from the process of transferring L-arginine into L-citrulline via a nitric oxide synthase (NOS). However, the detailed transferring mechanism of how to release the NO is still unclear till now. The NOS includes three kinds of isoforms, a neuronal NOS, an endothelial NOS and an immunologic NOS. The neuronal NOS and the endothelial NOS are constitutive forms, named as cNOS, whose activities are regulated by the calcium ion ($Ca^{++}$) and the calmodulin, and the concentration of the released NO is in the level of nano-molarity (nM). The immunologic NOS is an inducible form, named as iNOS, whose activity is not regulated by the $Ca^{++}$ and the calmodulin, and the concentration of the released NO is in the level of milli-molarity (mM). The genes of the cNOS and the iNOS are respectively located on different chromosomes. Taking human beings as an example, the neuronal NOS is located on the chromosome 12, the endothelial NOS is located on the chromosome 7, and the immunologic NOS is located on the chromosome 17 (Goldstein et al., 1996).

In retina, the NOS has been found in the retinal neuron, RPE, amacrine cells, ganglion cells, and Muller cells. It appears that the NO plays an important role in the physiology and pathology, and is closely related to the functions of the eye.

Because the NO can regulate the voltage-gated ion channel on the photoreceptors, it is conjectured that the NO is related to the transmission of the light messages. It's found that the NO owns the ability of regulating the blood flow of the retina under a basal condition or an ischemia environment (Tilton et al., 1993). Further, it's believed that the NO may own the ability of regulating the damage degrees of the blood vessels in the retina, in which the damage is caused by diabetes (Goureau et al., 1994). In addition, when the retinal glial cells and the RPE are stimulated by the LPS, IFN-g, and the TNF-a, the NOS will be largely expressed, which largely increase the production of the NO. In other words, under the conditions that the retina is inflamed or infected, the NO might play a role in the defense and protection mechanisms.

Till now, the position and the characteristics of the cNOS in the photoreceptor are still unclear. Some references disclose that the main body of the photoreceptor has the cNOS activities, and other references disclose that only the photoreceptor outer segments own the cNOS activities. The released NO can regulate the transmission of light, the transmitted message of the neutron synapase, and the blood flow of the retina under a physiological condition or an ischemia environment. The iNOS activity can also be found in some cells in the retina, such as the RPE and the Muller cells. In the culture of a bovine RPE, after being stimulated for 12 hours with the IFN-γ, LPS, and TNF-α, a mass of NO will be released for at least 96 hours. The effects of the cytokines on the RPE iNOS activity are quite complex. In a bovine RPE, for instance, being stimulated by the LPS and the IFN-γ, or the IFN-α are necessary for releasing a mass of NO. The bFGF inhibits the functions of NOS, but the TGF-β slightly enhances the functions of the NOS. For a human RPE, it is necessary to be stimulated by the Interleukin-1 β to release a mass of NO. However, the LPS is not the necessary factor to stimulate a human RPE. In addition, the TGF-β obviously inhibits the release of the NO in a human RPE.

When infected by bacteria, the expressions of iNOS may be beneficial because the released NO will kill the invaded microorganism. Contrarily, in some cases, when the released NO is exceeded, the released NO will result in the autoimmune diseases or the septic shock. In 1994, the first evidence for explaining the relationship between NO and the inflammation of the fundus oculi is proposed, and the reference also proposed that the uveitis resulted from the endotoxins can be blocked by the iNOS inhibitor. On the other hand, it appears that the aFGF and the bFGF can inhibit RPE from generating a mass of NO by treating the RPE with IFN-γ and LPS. Since it is the expression of the iNOS, but not the stabilities of the iNOS being mRNA, is inhibited, it's conjectured that the FGF will protect the RPE from being damaged by the endotoxins and the cytokines. Thus, it can be seen that the iNOS also plays a role in regulating the immunity of the retina.

The common retinal diseases include the proliferative diabetic retinopathy caused by the diabetes, the proliferative vitreoretinopathy, and the Aged-macular degeneration. However, the retinal diseases are the hardest diseases to cure in the ophthalmic defects. The hyperglycemia accelerates the glycation, which forms the advanced glycation end products (AGEs), and it is believed that the AGES closely relates to the vascular complication or the neuronal complication (Lu et al., 1998). An unstable schiff base is formed via the nonenzymatic reaction between the aldehyde group or the ketone group of the reducing sugar and the primary amino acids of the protein. Then, an amadori product is formed from the schiff base via the amadori rearrangement (Munch et al., 1997). And, the advanced glycosylation end product (AGE) will be formed from the amadori product via the rearrangement process. It is known that the nonenzymatic glycosylation is not a reversible reaction and usually occurs at the protein having a long half-life. While the AGE formation results in cross-linking, the protein molecule would have a resistance to the protease. Therefore, the accumulation of the AGE would be an aging mark (Handa et al., 1999). With the increasing age, the AGE amounts in the pyramidal neurons of the brain, the Bruch's membrane and the collagen will increase gradually. The reactive rate of the nonenzymatic glycosylation is a primary reaction, and the reaction rate is dependent on the concentrations of the reducing sugar and the protein. Usually, a diabetic patient has a higher blood glucose concentration than normal people, so that the glycosylation situation will be increased. It is known that the diabetic patients have higher probabilities of having some diseases or symptoms for the normal people are all directly related to the AGE, in which the disease or symptoms include the atherosclerosis, the kidney impair, the vessel damage, the neuron disease, the retinopathy, and the apoplexy (Zimmerman et al., 1995). The main reason for the aggregation of the erythrocyte, resulted from the diabetes, is that the tertiary structure of the albumin is changed after being glycosylated, so that the glycosylated albumin loses the functions of the anti-aggregation. Further, the reason for changing the permeability of the glomerulus is the glycosylation of the albumin but not the glycosylation of the glomerular basement membrane. In addition, the glycosylated protein has a better ability for penetrating the blood brain barrier.

The AGE can combine with some receptors on the cell surface or some proteins. The known receptors include the scavenger receptors type I, the scavenger receptors type II, the receptor for AGE (RAGE), OST-48 (AGE-R1), 80K-H phosphoprotein (AGE-R2), and the galectin-3 (AGE-R3). Besides, the RAGE can be found at the surfaces of the monocyte, the macrophage, the endothelial cell, and the glia cell. When the cell is activated by the AGE, the expressions of the extracellular matrix protein, the vascular adhesion molecules, and the growth factors will increase. Depending on the different cell types and the transmitted signals, some phenomena will occur accompanied with the above situation, such as the chemotaxis, the angiogenesis, the oxidative stress, the cell proliferation and the programmed cell death. It appears that the various cells in the human brain are able to express different RAGEs, which remove the AGE. When the remove ability is lost, the AGE will be accumulated outside the cell, which induces the inflammation reaction of the central nervous system. Furthermore, the AGE will induce the expressions of both the retinal vascular endothelial growth factor of the RPE and the PDGF-β (Handa et al., 1998). The AGE plays an important role in the aging process, so that designing a pathological model by the glycosylated albumin for developing a new medicine is very important.

The most important growth factor in the liver is the hepatocyte growth factor/scatter factor (HGF/SF), which is formed by combining the 60 KDa heavy chain (a chain) with the 30 KDa light chain (β chain) through the disulfide bond. The newly formed HGF/SF is the prepro HGF/SF, which needs to be modified by an enzyme for forming the heterodimeteric form before having a biological activity. The HGF is a multi-function growth factor, which not only has the ability for regulating the growth of the various cells, but also plays an important role in the tissue repair and the organ regeneration. The internal distribution of the HGF is very extensive, wherein the liver has the highest quantity of the HGF. Furthermore, the HGF can be found in the pancreas, the thymus, the blood, the small intestines, the placenta and so forth. In addition, the HGF/SF or the HGF/SF receptors are found in the eye secretions and the eye tissues, such as the tears, the lachrymal gland, and the cornea, so that it is conjectured that the HGF may play a role in the regulation of eyes (Li et al., 1996). Besides, it's known that the RPE has both the HGF and the HGF receptor (c-Met). Since the tyrosine phosphorylation of the c-Met expresses all the time, the HGF may be a growth factor with the self-stimulation function for the RPE. Further, the HGF may be related to the development of the retina (Sun et al., 1999), the wound healing, and the newborn retinal vessels (He et al., 1985).

From the above, it is known that RPE plays an important role in retinal regulation mechanisms. Meanwhile, we have found and proved that the Chinese herb, *Dendrobium* species, is able to enhance or inhibit some functions or regulation mechanisms in RPE. More specifically, the *Dendrobium* species can enhance the expressions of RPE phagocytosis, the NO formation of the RPE, the gene expressions of the RPE liver hepatocyte growth factor. The *Dendrobium* species can inhibit the gene expressions of the bFGF, the VEGF and the TGF-β in the RPE under a normal condition and an ischemia environment. Consequently, the relevant researches about the enhancing factors of the RPE activities are important for improving the health of the body. That is to say, the relevant research is absolutely worthy in the relevant industries.

Because of the technical defects described above, the applicant keeps on carving unflaggingly to develop "EXTRACT OF PLANT *DENDROBII CAULIS* AND PREPARING PROCESS THEREOF" through wholehearted experience and research.

SUMMARY OF THE INVENTION

It is a main object of the present invention to provide some experiment process for searching out the enhancing factors of the function or activity in the retinal pigment epithelium.

It is another object of the present invention to provide some enhancing factors of the function or activity in the retinal pigment epithelium for treating some ophthalmic defects.

It is another object of the present invention to provide some processes for testing the physiological ability of a plant extract.

It is an aspect of the present invention to provide an extract of a plant *Dendrobii Caadis*, obtained by an extraction of said plant or parts thereof with a water miscible organic solvent or a mixture thereof with water.

Preferably, the organic solvent is one selected from a group consisting of an alcohol having 1 to 8 carbon atoms, an alkane, and an ester.

In accordance with another aspect of the present invention, a physiological active composition including a physiologically acceptable carrier for carrying therewith, and one of an extract described above and an isomer of the extract is provided.

Preferably, the physiological active composition is a pharmaceutical composition.

Preferably, the physiologically acceptable carrier is a pharmaceutical carrier.

In accordance with another aspect of the present invention, a process for preparing an extract from a plant *Dendrobii Caulis*, including plural steps of extracting the plant or parts thereof with a water, a water miscible organic solvent or a mixture thereof is provided.

Preferably, the organic solvent is one selected from a group consisting of an alcohol having 1 to 8 carbon atoms, an alkane, and an ester.

In accordance with another aspect of the present invention, a process for preparing an extract from a plant is provided. The process includes steps of a) obtaining a first alcohol extract from the plant, b) extracting the first alcohol extract by a water and an alkane simultaneously for obtaining a first water layer and an alkane extract, c) extracting the first water layer by an ester for obtaining an ester extract and a second water layer, and d) extracting the second water layer by a second alcohol for obtaining a second alcohol extract and a third water layer.

Preferably, the plant belongs to Genus *Dendrobium*.

Preferably, the step a) further includes steps of a1) providing a dry material of the plant, a2) grinding the dry material by a pulverizer, and a3) extracting the ground dry material by the first alcohol for obtaining the first alcohol extract.

Preferably, the first alcohol is an alcohol having 1 to 8 carbon atoms.

Preferably, the second alcohol is an alcohol having 1 to 8 carbon atoms.

Preferably, the step b) further includes a step of b1) drying the first alcohol extract through steps of decompressing, condensing, and exhausting.

Preferably, the alkane extract is an n-hexane extract.

Preferably, the step c) further includes steps of c1) drying the ester extract, and c2) extracting the dried ester extract with a hexane and a methanol for obtaining a hexane extract and a methanol extract.

Preferably, the hexane extract is dried by steps of decompressing, condensing, and exhausting.

Preferably, the ester is an ethyl-acetate.

Preferably, the process further includes steps of e) chromatographing the second alcohol extract for obtaining a first eluate named as DCMPbL6,7, and f) chromatographing the DCMPbL6,7 by a mobile phase for obtaining a second eluate.

Preferably, the step e) is performed by an eluent of a methanol/water mixture in a 50:50 volume ratio.

Preferably, the mobile phase is an isopropanol/water mixture in a 20:80 volume ratio, and the second eluate is named as DCMPbL6,7D2.

Preferably, the DCMPbL6,7D2 is further chromatographed with a methanol/water/acetic acid mixture in a 35:65:1 volume ratio for obtaining a third eluate named as DCMPbL6,7D2H2.

Preferably, wherein the mobile phase is an isopropanol/water mixture in a 30:70 volume ratio, and the second eluate is named as DCMPbL6,7D3.

Preferably, the DCMPbL6,7D3 is further chromatographed with a methanol/water/acetic acid mixture in a 40:60:1 volume ratio for obtaining a fourth eluate named as DCMPbL6,7D3H3.

Preferably, the mobile phase is an isopropanol/water mixture in a 40:60 volume ratio, and the second eluate is named as DCMPbL6,7D4.

Preferably, the DCMPbL6,7D4 is chromatographed with a methanol/water/acetic acid mixture in a 45:55:1 volume ratio for obtaining a fifth eluate named as DCMPbL6,7D4H3.

In accordance with another aspect of the present invention, an extract obtained according to the process described above is provided.

In accordance with another aspect of the present invention, a physiological active composition including a physiologically acceptable carrier for carrying therewith, and one of an extract according to the process described above and an isomer of the extract is provided.

Preferably, wherein the physiological active composition is a pharmaceutical composition.

Preferably, the physiologically acceptable carrier is a pharmaceutical carrier.

In accordance with another aspect of the present invention, an eluate being the second eluate obtained according to the process described above is provided.

In accordance with another aspect of the present invention, a physiological active composition including a physiologically acceptable carrier for carrying therewith, and one of the eluate being the second eluate described above and the isomer of the eluate is provided.

Preferably, the physiological active composition is a pharmaceutical composition.

Preferably, the physiologically acceptable carrier is a pharmaceutical carrier.

In accordance with another aspect of the present invention, another eluate being the third eluate according to the process described above is provided.

In accordance with another aspect of the present invention, a physiological active composition including a physiologically acceptable carrier for carrying therewith, and one of the eluate being the third eluate described above and the isomer of the extract is provided.

Preferably, the physiological active composition is a pharmaceutical composition.

Preferably, the physiologically acceptable carrier is a pharmaceutical carrier.

In accordance with another aspect of the present invention, an eluate being the fourth eluate according to the process described above is provided.

In accordance with another aspect of the present invention, a physiological active composition including a physiologically acceptable carrier for carrying therewith, and the eluate being the fourth eluate and the isomer of the eluate is provided.

Preferably, the physiological active composition is a pharmaceutical composition.

Preferably, the physiologically acceptable carrier is a pharmaceutical carrier.

In accordance with another aspect of the present invention, an eluate being the fifth eluate according to the process described above is provided.

In accordance with another aspect of the present invention, a physiological active composition including a physiologically acceptable carrier for carrying therewith, and one of an eluate according to the fifth elute and the isomer of the eluate is provided.

Preferably, the physiological active composition is a pharmaceutical composition.

Preferably, the physiologically acceptable carrier is a pharmaceutical carrier.

In accordance with another aspect of the present invention, a process for preparing an extract from a plant is provided. The process includes steps of a) obtaining a first organic extract from the plant, b) extracting the first organic extract by a water and a second organic solvent simultaneously for obtaining a first water layer and a second organic extract, c) extracting the first water layer by a third organic solvent for obtaining a third organic extract and a second water layer, and d) extracting the second water layer by a four organic solvent for obtaining a fourth organic extract and a third water layer.

Preferably, the plant is an orchid.

Preferably, the step a) further includes steps of a1) providing a dry material of the plant, a2) grinding the dry material by a pulverizer, and a3) extracting the ground dry material by the first organic solvent for obtaining the first alcohol extract.

Preferably, the first organic solvent is an alcohol having 1 to 8 carbon atoms.

Preferably, the second organic solvent is an alkane having 1 to 8 carbons.

Preferably, the third organic solvent is an ester.

Preferably, the fourth organic solvent is an alcohol having 1 to 8 carbon atoms.

In accordance with another aspect of the present invention, a substance defined by the following FIGS. 5 to 11 is provided.

In accordance with another aspect of the present invention, a physiological active composition including a physiologically acceptable carrier for carrying therewith, and one of a substance according to FIGS. 5 to 11 and an isomer of the substance.

Preferably, the physiological active composition is a pharmaceutical composition.

Preferably, wherein the physiologically acceptable carrier is a pharmaceutical carrier.

In accordance with another aspect of the present invention, a substance defined by the following FIGS. 13 to 17 is provided.

In accordance with another aspect of the present invention, a physiological active composition including a physiologically acceptable carrier for carrying therewith, and one of a substance according to FIGS. 13 to 17 and an isomer of the substance is provided.

Preferably, the physiological active composition is a pharmaceutical composition.

Preferably, the physiologically acceptable carrier is a pharmaceutical carrier.

In accordance with another aspect of the present invention, a substance defined by the following FIGS. 19 to 24 is provided.

In accordance with another aspect of the present invention, a physiological active composition including a physiologically acceptable carrier for carrying therewith, and one of a substance according to FIGS. 19 to 24 and an isomer of the substance.

Preferably, the physiological active composition is a pharmaceutical composition.

Preferably, the physiologically acceptable carrier is a pharmaceutical carrier.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
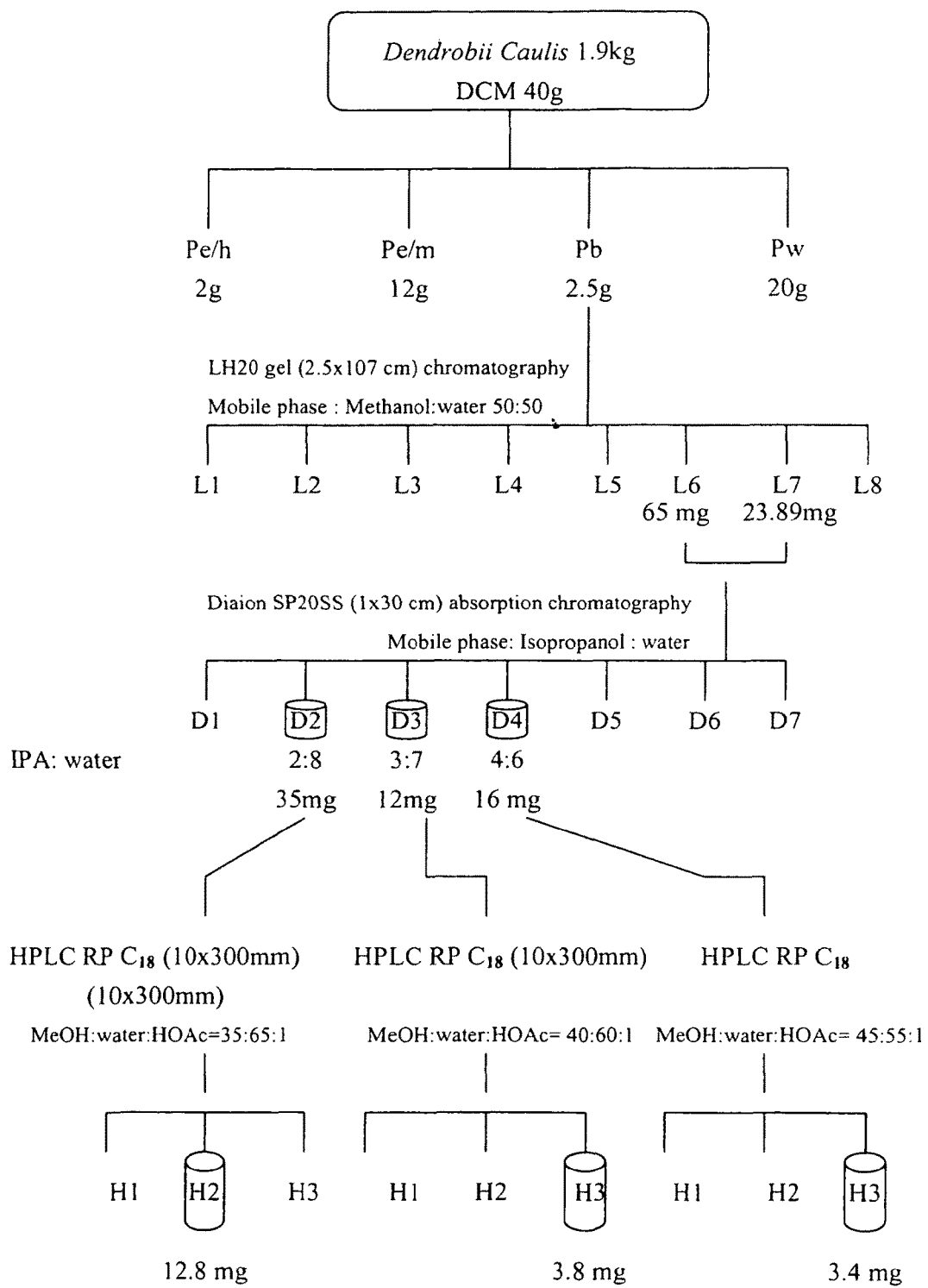
FIG. 1 is the flow chart of separating protocol for *Dendrobii Caulis* extract according to a preferred embodiment of the present invention.

The present invention will now be described more specifically with reference to the following embodiments.

EXAMPLE I

Culturing of the Retinal Pigment Epithelium.

The fresh bovine eyes are collected from a slaughterhouse within 2-3 hr after slaughtering. The surfaces of the bovine eyes are sterilized with the tincture of iodine, and then are washed with the PBS (phosphate-buffer saline) buffer solution twice. After dissecting the bovine eyes and removing the lens, the vitreous body, and the retina in sequence, the dissected eyes are treated with 0.01% EDTA (ethylene diamine tetra-acetic acid) for 40 min and then 5% trypsin for 15 min. Then, a single RPE can be obtained after slightly pressing the eyes with a tweezers with round tips and pipetting several times. The pipetted solution is placed within the DMEM (Dulbecco's Modified Eagle Media) containing 10% FCS (fetal calf serum), and then is incubated in an incubator with a humidified atmosphere with 5% $CO_2$ at 37° C. The medium is replaced per 5-6 days till the cells reach the confluency. The cells are subcultured with a medium containing 0.05% trypsin and 0.02% EDTA. The fifth and the sixth generations of the cells are the main objects of the present invention for the bioactivity testing.

EXAMPLE II

Preparation of the Rod Outer Segments (ROS).

Fresh bovine eyes are kept on ice and exposed under a light for 30 min after obtaining from the slaughterhouse. The surfaces of the bovine eyes are sterilized with the tincture of iodine, and then are washed with the Hank's buffer solution twice. After dissecting the bovine eyes and removing the lens, and the vitreous body in sequence, the retina are taken out and cut into pieces and then treated with 20 mM Tris-HCl containing 20% sucrose. After stirred for 3 hrs at 4° C., the cell solution is filtered with filters of pore size of 300, 220, 110, 74, 53, and 10 mesh respectively. After counting the cell numbers, the cells are aliquoted with a number of 1×10$^8$ ROS cells per column, and the columns are stored in a refrigerator at −20° C.

EXAMPLE III

Preparation of the FITC (Fluorescein Isothiocyanate)-ROS.

After the stored ROS cell solution is unfrozen and the suspension is removed, the unfrozen cell solution is mixed with 700 μl Borate buffer (pH 8.0), containing 10% sucrose and some FITC powder with a 1/1000 weight of the ROS is added. Then, the cell solution is stirred for 1.5 hrs at 4° C. The uncombined FITC without attached on the ROS is removed by washing with 20 mM Trans-acetate (pH 7.2) containing 20% sucrose. The cell solution is then centrifuged for 10 min at 10000 rpm. The relevant steps described above are repeated several times. Finally, the pellet is dissolved in the DMEM containing 2.5% sucrose.

EXAMPLE IV

Testing the Phagocytosis Function of RPE.

The content of the RPE is set up at a concentration of $5 \times 10^4$ cells/ml, and then 200 μl RPE is seeded into 96 well plates. After the cells reach the confluency, the medium is replaced. Then, 20 μl of various testing medicine is added into each well under the condition that the concentration of the fetal bovine serum is ranged from 2% to 5%. After incubating for 48 hrs, 50 μl of $2 \times 10^7$ FITC-ROS/ml is added into each well, and the culture is incubated for 4 hrs. The supernatant is removed, and the pellet is washed with 2.5% sucrose/PBS for several times. Finally, 100 μl PBS is added, and the cell number is measured by the Cyto-Fluorometer (Ex filter: 485/20 nm, Em filter 530/25 nm). The detected value is the cell number of the FITC-ROS attached on the RPE surface and the phagocytized FITC-ROS. Each well is added with 5 μl FluoroQuench and then is incubated in an incubator for 1 hr. Next, the relevant fluorescence value is measured and is thought as the cell number of the phagocytized FITC-ROS.

EXAMPLE V

An Assay for the NO formation of RPE

100 μl of the supernatant of the cell solution is mixed with 50 μl 2,3-diaminonaphthalene (DAN). After reacting for 10 min at room temperature, the supernatant is added with 25 μl 12.8N NaOH for terminating the reaction, and then is tested with the Cyto-Fluorometer 2300 (basic state: 360+40 nm, excited state: 460+40 nm). The measured value can be converted into the corresponding NO concentration via a standard curve obtained from $NaNO_2$ with known concentration.

EXAMPLE VI

Preparation of the RPE RNA

The RPE is incubated in the 100 mm culture plate ($1 \times 10^6$ cells in DMEM+10% FCS). After the cells reach the cofluency, the culturing medium is replaced with the DMEM containing 2.5% FCS therein. Next, 0.1 μg/ml of the *Dendrobii Caulis* distribution obtained by extracting with several chemical solvates is added. After incubating for 48 hrs, the culturing medium is removed and the cells are washed with ice PBS buffer solution twice. Then, 1 ml/$10^5 \sim 10^6$ cells of RNAzol™ B is added, and the cell solution is placed under room temperature for 5 min. The cells are scraped from the culture plate by a scraper, and then are placed into a 1.5 ml centrifuge tube. After adding the chloroform having 1/10 volume amount of the cell, the cell solution is mixed immediately and placed on the ice for 5 min. The cell solution is centrifuged at 4° C. for 15 min at 12000 rpm, and then the upper transparent water layer is removed into another 1.5 ml centrifuge tube. After adding the isopropanol having the same volume amount of the water layer, the solution is mixed immediately and placed on the ice for 5 min. The cell solution is centrifuged at 4° C., for 10 mins at 12000 rpm, and then the supernatant is discarded. The precipitate is washed with 70% ethanol, and then is centrifuged for 8 min at 7500 rpm, at 4° C. After removing the ethanol and drying the precipitate, the dried precipitate is dissolved with excess pure water (mini-Q water) containing 0.1% DEPC. Some solution is quantitated by the $OD_{260}$, and the corresponding purity is determined by the $OD_{260}/OD_{280}$. The rest of the solution is stored within 70% ethanol at $-20°$ C.

EXAMPLE VII

The Reverse Transcription and Polymerase Chain Reaction (RT-PCR) of the RPE Growth Factor There are two total RNA samples extracted from different RPE, the experimental set and the control set. In which, the experimental set is treated with the previously mentioned testing medicine. 2.5 μg oligo dT is added into the reaction tube containing 5 μg of the extracted total RNA. After being incubated for 10 min at 70° C., the reaction solution is placed for another 10 min at room temperature. Then, 1 μl (10 unit) reagents of 10 mM dNTP 2 μl, rRNasin 1 μl, AMV (Avian Myeloblastosis virus) reverse transcriptase and the reaction buffer solution are added into the reaction solution, which makes the reaction solution with a total volume of 20 μl. Next, the solution is reacted at 42° C. for 50 min, at 90° C. for 5 min, and then placed on the ice for 10 min. The reaction solution is added with 1 μl rRNAaseH, and is reacted at 37° C. for 30 min. After obtaining cDNA, 5 μl of the 2 mM dNTP is added into the reaction tube containing the cDNA obtained from the reverse transcription reaction in which the cDNA has various diluted concentrations. 1 μl sense primer and 1 μl antisense primer designed according to the desired testing targets, both have the concentration of 0.1 μg/μl, are added into the reaction tube. In which, the designed is one selected from a group consisting of the β-actin (for internal control), the HGF primer, the VEGF primer, the bFGF primer, and the TGF-β primer. And, the target genes are HGF, VEGF, bFGF, and TGF-β. 1 μl polymerase (2 unit) and the reaction buffer are added into the reaction solution for making a total volume of 20 μl. Then, the polymerase chain reaction is proceeded in the DNA thermal cycler (Perkin-Elmer-Cetus). In which, the reaction conditions for denaturing, annealing, and extension are respectively at 94° C. and at 57° C. for 1.5 mins, and at 72° C. for 2 mins. The PCR running cycles for the β-actin, HGF, VEGF, bFGF, and TGF-β are 25, 35, 25, 25, and 25 cycles respectively.

The following are the descriptions of the primers.

```
1. HGF primers (Gibco, Gaithersburg, MD, USA)
     Sense, 21 mer: 5'-GGG ATT CTC AGT ATC CTC ACA-3'
     Antisense, 21 mer: 5'-CCT ACA TTT GTT CGT GTT GGA-3'

2. VEGF primer:
     Sense, 24 mer: 5'-AGA AAC CCC ACG AAG TGG TGA AGT-3'
     Antisense, 24 mer: 5'-CGT TTA ACT CAA GCT GCC TCG CCT-3'

3. bFGF primer:
     Sense, 19 mer: 5'-CCA AGC GGC TGT ACT GCA A-3'
     Antisense, 24 mer: 5'-GAT CAG ATG CTG CCA TTA AGA TCA-3'
```

```
4. TGF-β primer:
   Sense, 24-mer: 5'-CCT GGA CAC CAA CTA CTG CTT CAG-3'
   Antisense, 24-mer: 5'-ACG ATC ATG TTG GAC AAC TGC TCC-3'
```

EXAMPLE VIII

Preparation of the Glycated Albumin
(a) Preparation of the Bovine Glycated Albumin The bovine glycated albumin (fraction V) is diluted with 1×PBS (pH 7.4) for forming a 1 mM reaction solution. The reaction solution is filtered through the aseptic 0.22 μm membrane and is then added with 250 mM glucose which has been filtered through the aseptic 0.22 μm-membrane. Then, the reaction solution is incubated in the incubator at 37° C. for the glycosylation process. After 3 weeks, the excess glucose of the reaction solution is removed by dialysis. The obtained solution is purified by the Cona-Sepharose gel, and then is treated with the following steps of dialyzing, lyophilizing and storing.
(b) Preparation of the Mice Glycated Albumin.

The mice glycated albumin (fraction V) is diluted with 1×PBS (pH 7.4) for forming a 100 mg/ml (1.51 mM) reaction solution. The reaction solution is filtered through the aseptic 0.22 μm membrane and is then added with 1.8 g/ml (1M) D-glucose, which has been dissolved in the 1×PBS with a volume ratio 1:1 and filtered through the aseptic 0.22 μm membrane. Then, the reaction solution is incubated in the incubator in the dark at 37° C. for glycosylation process. After 60 days, the excess glucose of the reaction solution is removed by dialyzing with a dialysis bag. The obtained solution is filtered through the aseptic 0.22 gm membrane, and then the solution is respectively aliquoted after the protein concentration is detected. After lyophilizing, the aliquoted reaction solution is stored at −20° C.

EXAMPLE IX

Determination of AGE-BSA by FITC Test 100 mg glycated albumin and 1.8 mg FITC are dissolved in 15 ml 0.1M sodium carbonate buffer, pH 9.5. Under dark environment, after being stirred for 5 hours at 25° C., the reaction solution is chromatographed with a HW-55F (1.6× 100 cm) molecule sieve column, the elution buffer is 5% n-butanol (v/v), and the chromatographic rate is determined only by gravity. After being dialyzed three times with de-ionized water, and the protein concentration of the obtained solution is detected. Then, the solution is filtered through the aseptic membrane and respectively aliquoted, lyophilized. After the fluorescence of the solution is determined, the equivalent ratio of the solution marked with fluorescence is estimated.

EXAMPLE X

Observation of the Degradation of FITC-Labeled AGE-BSA by RPE Cells.

First, a pre-sterilized cover slide is put into each well of the 24 well culture plate in advance, and then 300 μl 0.5% gelatin is coated on the plate for 30 min. Secondly, the coated gelatin is washed by the medium. Then, $5 \times 10^4$ RPE cells/well are seeded into the 24 well plate and cultured with 10% FCS/DMEM solution, while each well contains 0.7 ml medium therein. After 48 hours, when the well is filled with cells, the culture solution is discarded. After being washed with 0.5 ml medium for three times, 0.5 ml of the FITC-BSA DMEM solution having various concentration, 30-300 ug/ml, is added. Then, the cells are washed with PBS solution four times for removing the un-phagocytized and combined fluorescence. The cover slide is taken out from the cell and moistened with PBS solution containing 1% FQEB. After being sealed, the cover slide is observed under a fluorescence microscope at once.

EXAMPLE XI

Enhancement of the *Dendrobii Caulis* Crude Extract for Acceleratively Degrading the Albumin Glycosylation of RPE.

$1 \times 10^6$ RPE cells are seeded into the 96-well microplate, containing 10% FCS in DMEM, at 37° C., supplied with 5% $CO_2$. After incubation of 48 hrs, five sets of experiment are treated with the *Dendrobii Caulis* crude extract, in which each set of experiment includes two microplates for different treating time. After treating for 36 or 48 hrs, 0.01% EDTA is added into the microplate for harvesting the cells, and then the cells are suspended in the DMEM cell number for counting. Then, the cell solution is centrifuged for 5 min at 1200 rpm, and the cells are suspended back into 10 ml DEME twice. Then, the cell solution is centrifuged again, and is suspended back again with the 0.7 ml Homogenization buffer (50 mM sodium acetate buffer, pH4.5, 1 mM DTT, 0.15M NaCl, 3 mM $NaN_3$) containing 0.1% TritonX-100. Then, the cell solution is vibrated by a sonicator for 15 sec, four cycles, for breaking the cell completely. Next, the cell solution is centrifuged at 13000 rpm for 15 mins, vibrated by a sonicator for 15 sec, four cycles, and centrifuged again at 11000 rpm for 15 min. The supernatant is then collected and filtrated under an aseptic condition. The protein concentration is detected. 1000 μg/ml AGE-BSA are filtrated under an aseptic condition. After reacting for 0, 6, 12, 24, 48, 72 hrs, the corresponding electrophoresis is proceeded in order to observe the conformation and the degree of the AGE-BSA degradation

EXAMPLE XII

Preparation of the *Dendrobii Caulis* Extract and Separation of the Purified Active Content Thereof
Preparation of the *Dendrobii Caulis* Alcohol Extract.

2 kg dry *Dendrobii Caulis* is ground by a pulverizer. Then, the ground material is put into a bottle containing the methanol or ethanol, and immersed overnight. The reaction solution is filtrated by a gas-extracting apparatus for obtaining the filtrate. Then, the filtrate is put back into the bottle for re-concentration, and some amount of methanol or ethanol is added therein for immersing overnight. Filtrate the reaction solution again. The same protocols are repeated for three times. All the filtrates are then collected, and the methanol or ethanol is exhausted completely. The obtained *Dendrobii Caulis* alcohol crude extract is named as DeCaM. (c) Extraction and separation of the *Dendrobii Caulis* purified component.

Please refer to FIG. 1. FIG. 1 is the flow chart of the separating protocol for *Dendrobii Caulis* extract according to a preferred embodiment of the present invention. Three active components are separated from *Dendrobii Caulis*. 1.9 kg *Dendrobii Caulis* is extracted by methanol three times for obtaining the methanol extract of *Dendrobii Caulis*. The methanol extract of *Dendrobii Caulis* is then re-concentrated and completely dried for forming the DCM standard. The dry DCM standard is dissolved in 2 L EtOAc and then partitioned with 2 L water for obtaining an EtOAc layer and a first water layer. The water layer is extracted with 2 L EtOAc two more times. All the EtOAc layers are collected, re-concentrated and completely dried for obtaining the EtOAc extract. The dry EtOAc extract is respectively partitioned three times with 4 L hexane and 2 L methanol for obtaining a hexane layer and a methanol layer. After re-concentrated and dried, the dried hexane layer and methanol layer are named as DCMPe/h standard (Pe/h), and DCMPe/m standard (Pe/m) respectively. In addition, the first water layer is adjusted into 2 L volume by adding de-ionized water, and then is partitioned by adding 2 L butanol for obtaining a butanol layer and a second water layer. After re-concentrated and dried the dried butanol layer and the second water layer are named as DCMPb standard (Pb), and DCMPw standard (Pw) respectively. The Pb is extracted by LH20 gel chromatography with a molecule column (2.5× 107 cm, mobile phase <methanol:$H_2O$=50:50>). After the activity screening, the DCMPbL6,7 samples are obtained. Then, the samples DCMPbL6,7 are extracted by the Diaion SP-20 SS chromatography with y a absorption column (1×30 cm). When the mobile phase is isopropanol:$H_2O$=0.20:80, the eluate named as DCMPbL6,7D2 can be obtained. When the mobile phase is isopropanol:$H_2O$=30:70, the eluate named as DCMPbL6,7D3 can be obtained. When the mobile phase is isopropanol:$H_2O$=40:60, the eluate named as DCMPbL6,7D4 can be obtained. Then, the DCMPbL6,7D2 is chromatographed by HPLC reverse C18 column (10×300 mm) with the mobile phase of methanol:$H_2O$:acetic acid=35:65:1, and the eluate named as DCMPbL6,7D2H2 is obtained. Further, the DCMPbL6,7D3 is chromatographed by HPLC reverse C18 column (10×300 mm) with the mobile phase of methanol:$H_2O$:acetic acid=40:60:1, and the eluate named as DCMPbL6,7D3H3 is obtained. Further, the DCMPbL6,7D4 is chromatographed by HPLC reverse C18 column (10×300 mm) with the mobile phase of methanol:$H_2O$:acetic acid=45:55:1, and the eluate named as DCMPbL6,7D4H4 is obtained.

(b) Preparation of the *Dendrobii Caulis* Chemical Solvent Extract.

The DCM (extracts of *Dendrobii Caulis* extracting with methanol) is dissolved in 400 ml de-ionized water, and then 400 ml n-hexane is added. The reaction solution is partitioned for obtaining the n-hexane layer and the first water layer respectively. The related extraction steps are repeated three times. The final n-hexane layer is named as DCMph. The first water layer is then partitioned with the ethyl-acetate four times for obtaining a second water layer and a EtOAc layer. The obtained EtOAc layer is named as DCMPe. Then, the second water layer is partitioned with the n-butanol three times for obtaining an n-butanol layer named as DCMPb and a third water layer named as DCMPw.

EXAMPLE XIII

Effect of the Alcohol Extract of *Dendrobii Caulis* on the Mice Having Diabetic Angiopathy Induced by the Glycated Albumin.

Four sets of BABLC/c mice, aged 8 weeks, are fed with the forage containing various amount of the methanol extract of *Dendrobii Caulis*, 0 mg/kg/day, 1 g/kg/day, 200 mg/kg/day, 40 mg/kg/day. Each set has three mice. The mice are treated with glycated mice serum albumin (MAG) via the tail vein injection, 2.5 mg/time, twice/week, for three weeks. Then, the mice are continuously fed with the forage containing the methanol extract of *Dendrobii Caulis* for two weeks. The mice are dissected in order to prepare wax-embedded sections of the eyes, liver, and kidney in which the pathological change are observed by the HE stain.

EXAMPLE XIV

Effects of the Extract and Purified Component of *Dendrobii Cauli* on RPE Function Phagocytosis.

Figure 2:
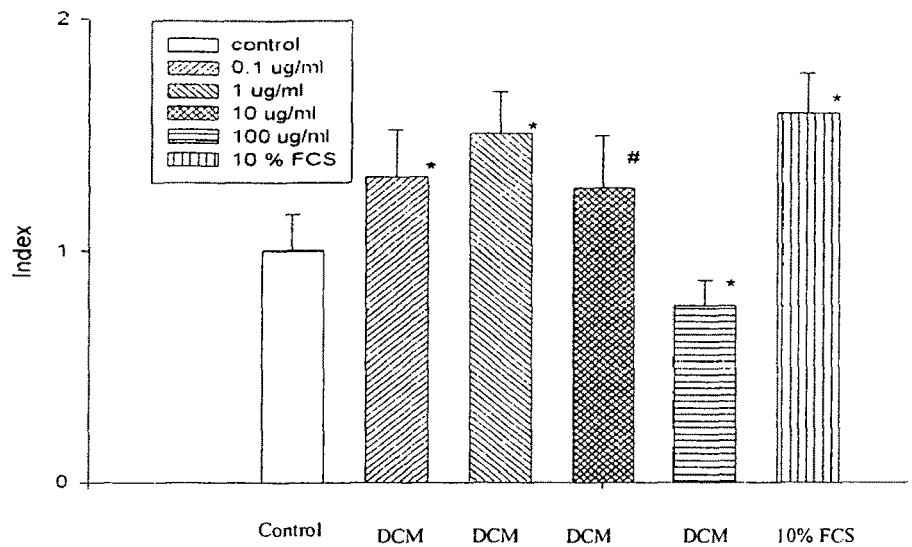
FIG. 2 is the bar chart illustrating the effects of the methanol extract of *Dendrobii Cauli* on the RPE function phagocytosis according to a preferred embodiment of the present invention.

Please refer to FIG. 2, which is the bar chart illustrating the effects of the methanol extract of *Dendrobii Cauli* on the RPE function phagocytosis. As shown in FIG. 2, it's known that various concentrations (0.1, 1, 10 µg/ml) of the methanol (DCM) extract of *Dendrobii Cauli* can accelerate the phagocytosis of RPE. The relevant experimental contents are simply described as follows. $1 \times 10^4$ RPE cells are seeded in 96-well microplate per well, containing 10% FCS in DMEM after 48 hrs, and the medium is changed with 2% FCS in DMEM. Then different concentrations of the methanol extract of *Dendrobii Caulis* are added respectively. After 48 hrs, 50 µl of $2 \times 10^7$ FITC-ROS/ml is added into each well. Four hours later, the unbounded FITC-ROS is washed out with PBS. The fluorescence intensity is detected by a 1420 Multilable counter (PE) measurement system. # $P<0.05$,* $P<0.01$ are obtained by comparing with phagocytosis of RPE treated with 2% FCS.

Figure 3:
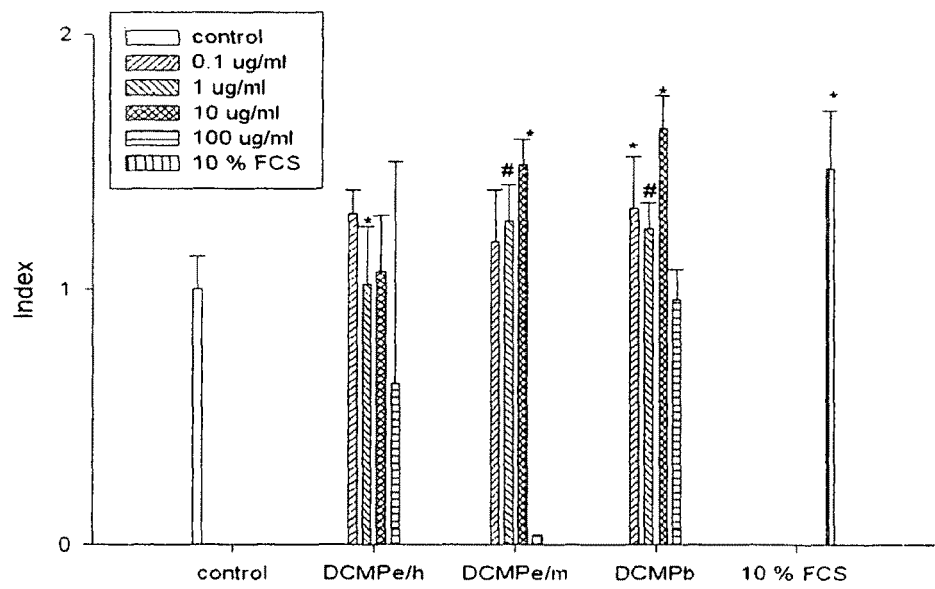
FIG. 3 is the bar chart illustrating the effects of the solvent partition extracts of *Dendrobii Cauli* on the phagocytosis of RPE according to a preferred embodiment of the present invention.

Please refer to FIG. 3, which is the bar chart illustrating the effects of the solvent partition extracts of *Dendrobii Cauli* on the phagocytosis of RPE. As shown in FIG. 3, it is clear that the DCMPe/m partition and the DCMPb partition can significantly accelerate the phagocytosis of RPE. The relevant experimental contents are simply described as follows. $1 \times 10^4$ RPE cells are seeded in 96-well microplate per well, containing 10% FCS in DMEM. After 48 hrs, the medium is changed with 2% FCS in DMEM and then different concentrations of the extract of *Dendrobii Caulis* (DCMPe/h, DMCPe/m and DCMPb) are added respectively. After 48 hrs, 50 µl of $2 \times 10^7$ FITC-ROS/ml is added to each well. Four hours later, the unbounded FITC-ROS is washed out with PBS. The fluorescence intensity is detected by a 1420 Multilable counter (PE) measurement system. # $P<0.05$,* $P<0.01$ are obtained by comparing with phagocytosis of RPE treated with 2% FCS.

Figure 4:
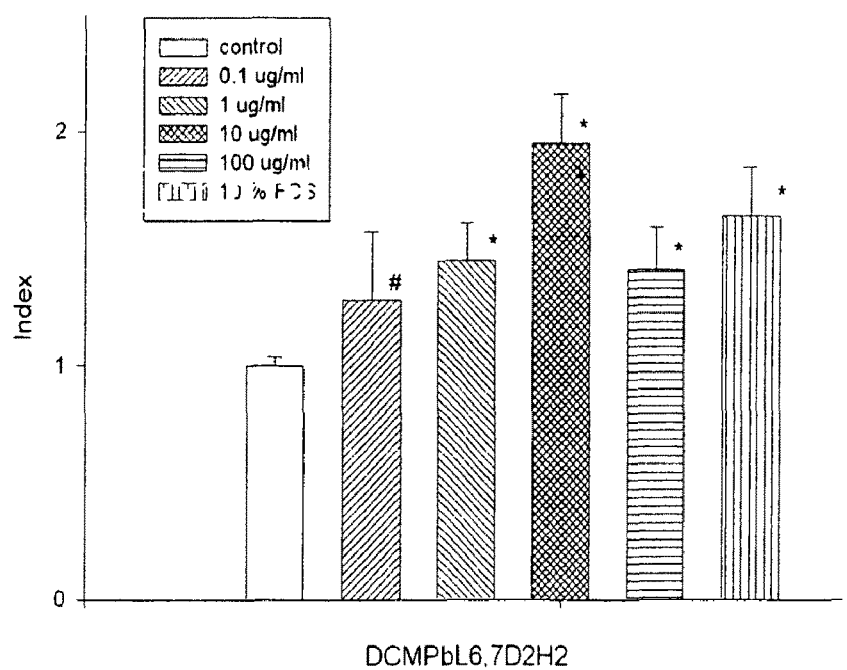
FIG. 4 is the bar chart illustrating the effects of DCMPbL6, 7D2H2 on phagocytosis of RPE according to a preferred embodiment of the present invention.
Figure 5:
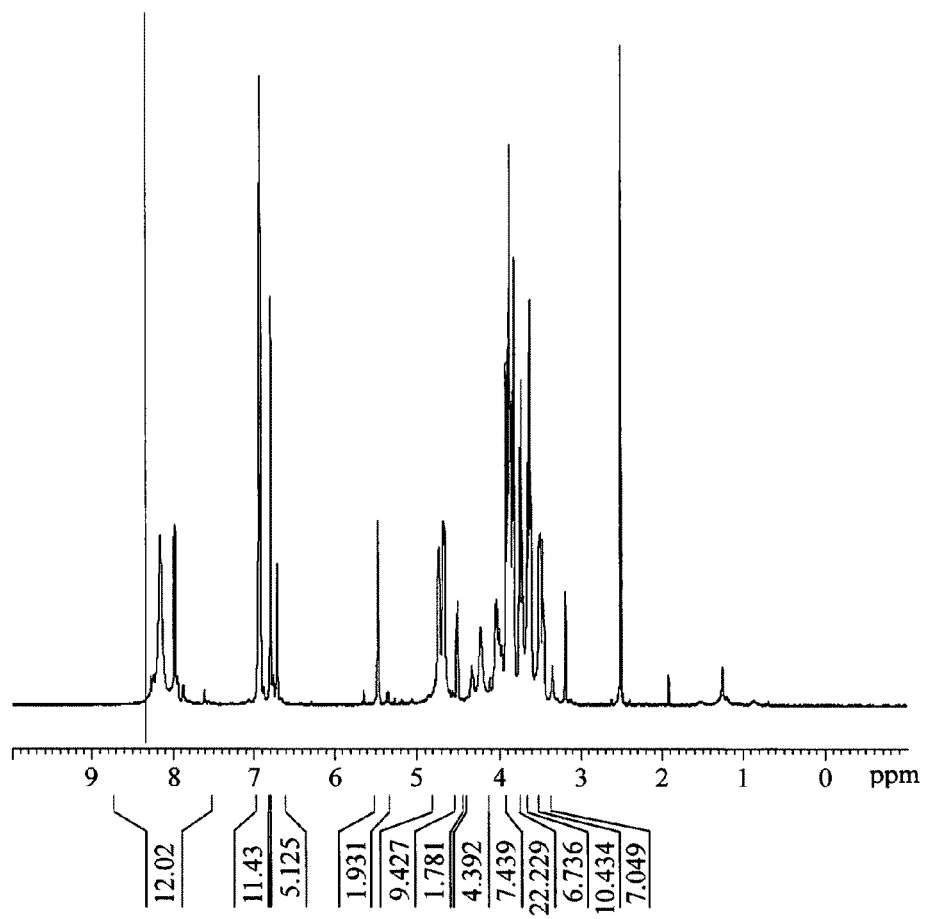
FIG. 5 shows the $^1$H-NMR spectrum of DCMPbL6,7D2H2 in the solvents of Methanol-$d_4$ and DMSO-$d_6$, using a 600-MHz instrument according to a preferred embodiment of the present invention.
Figure 6:
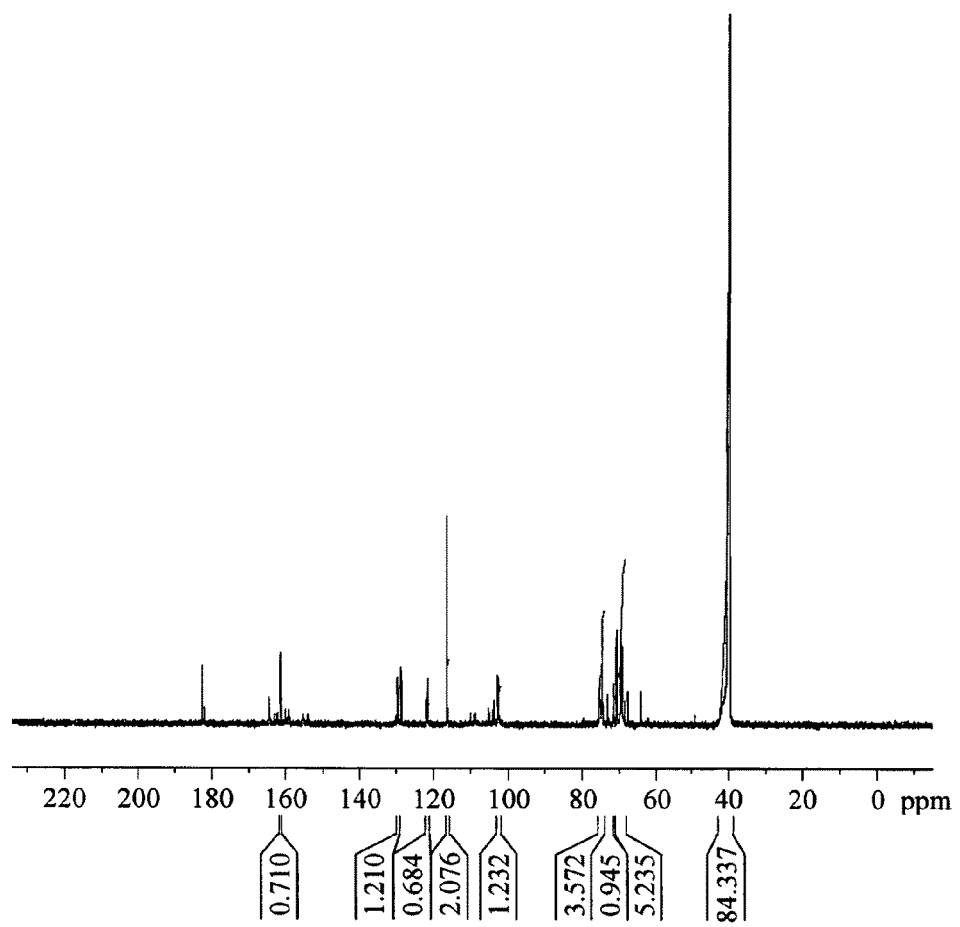
FIG. 6 shows the $^{13}$C-NMR spectrum of DCMPbL6, 7D2H2 in the solvents of Methanol-$d_4$ and DMSO-$d_6$, using a 600-MHz instrument according to a preferred embodiment of the present invention.
Figure 7:
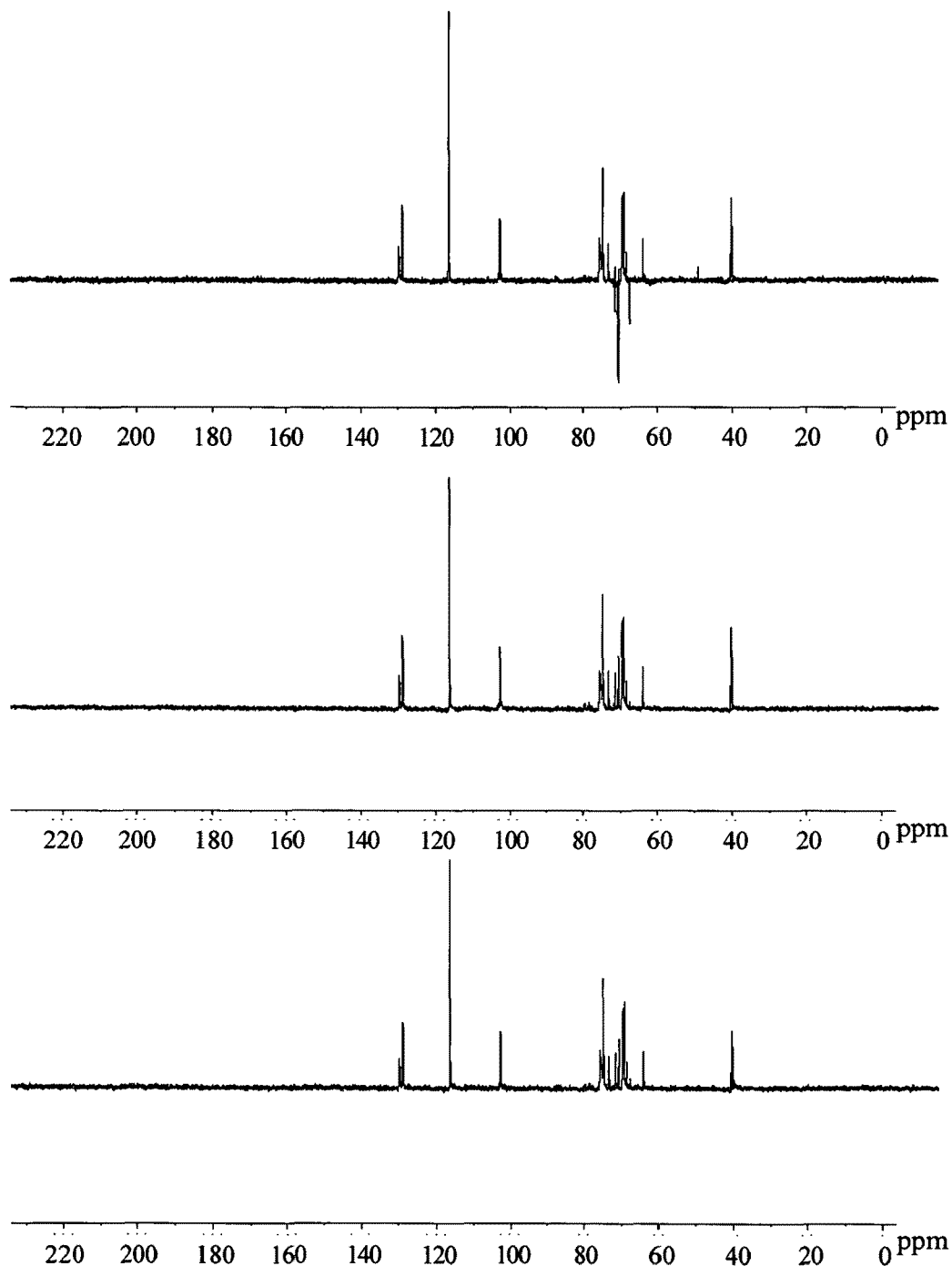
FIG. 7 shows the DEPT spectrum of DCMPbL6,7D2H2 in the solvents of Methanol-$d_4$ and DMSO-$d_6$, using a 600-MHz instrument according to a preferred embodiment of the present invention.
Figure 8:
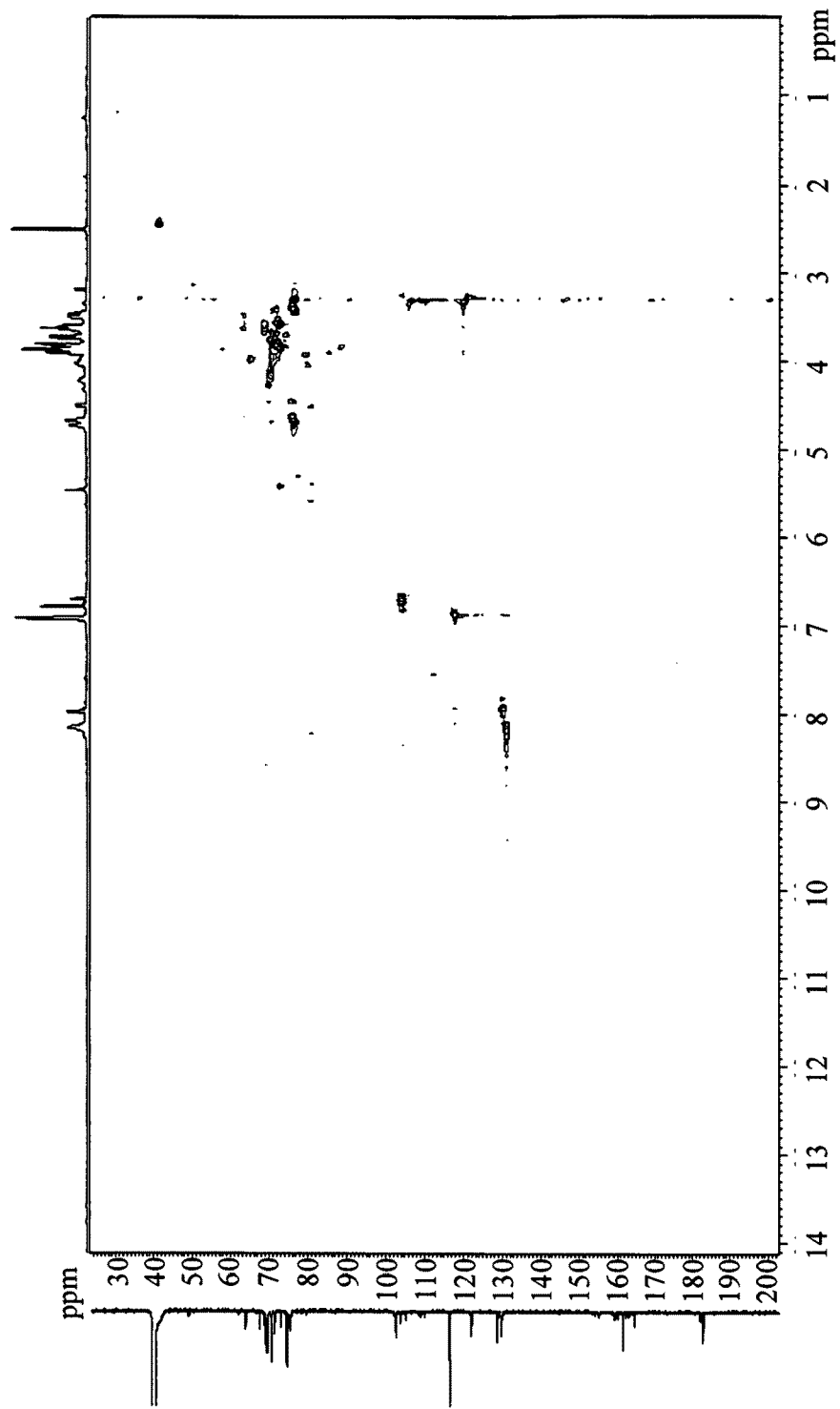
FIG. 8 shows the HMQC spectrum of DCMPbL6,7D2H2 in the solvents of Methanol-$d_4$ and DMSO-$d_6$, using a 600-MHz instrument according to a preferred embodiment of the present invention.
Figure 9:
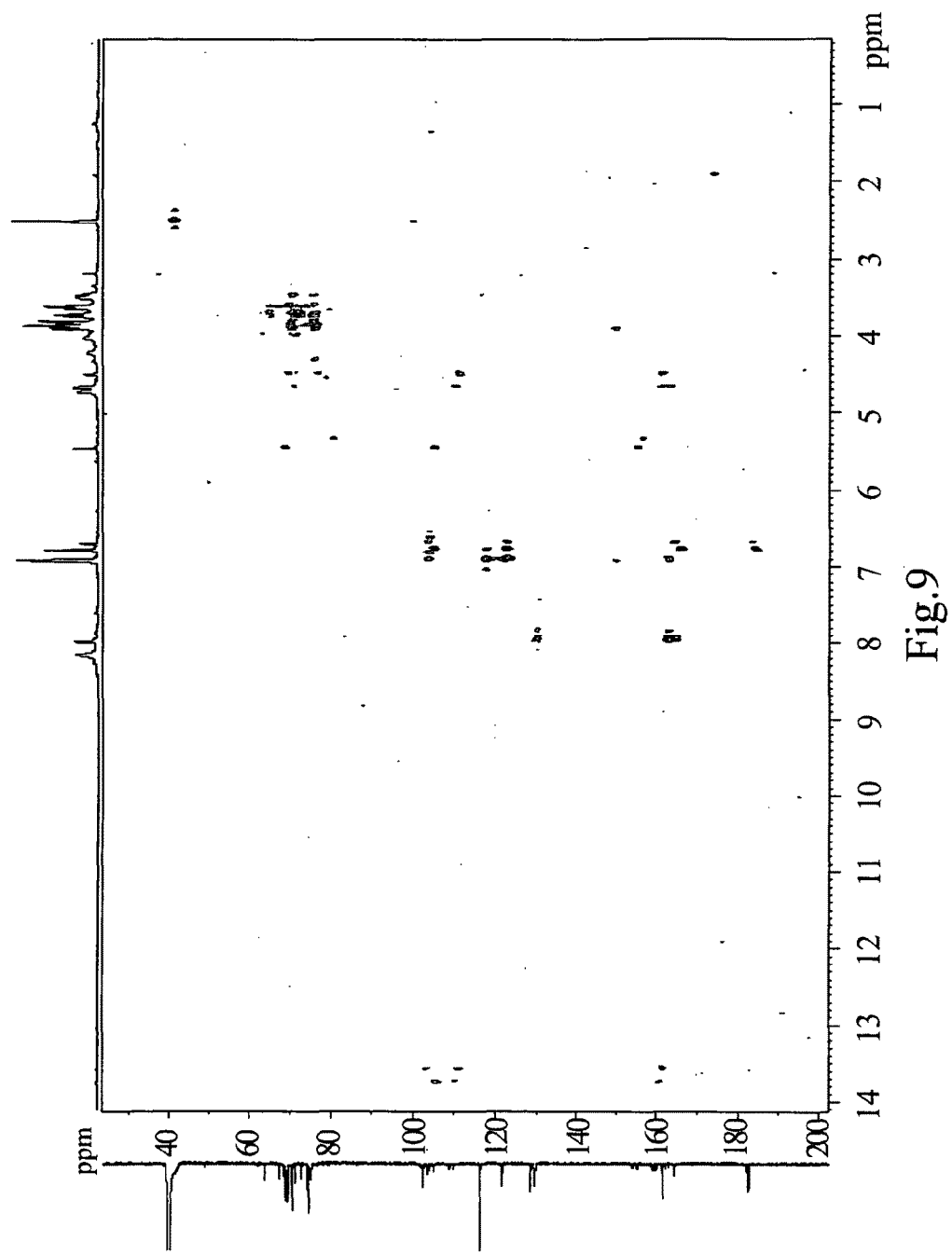
FIG. 9 shows the HMBC spectrum of DCMPbL6,7D2H2 in the solvents of Methanol-$d_4$ and DMSO-$d_6$, using a 600-MHz instrument according to a preferred embodiment of the present invention.
Figure 10:
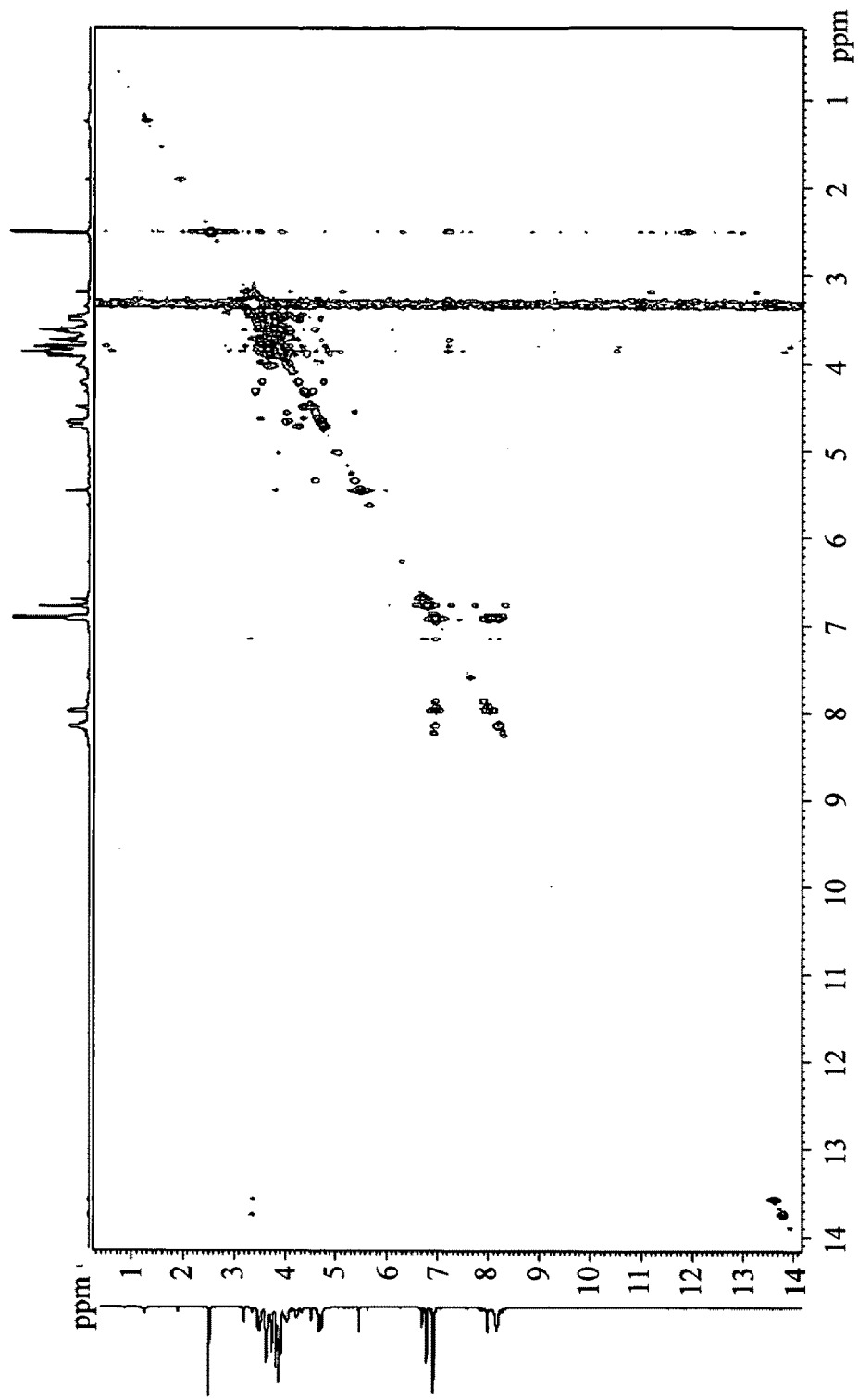
FIG. 10 shows the $^1$H-$^1$H COSY spectrum of DCMPbL6, 7D2H2 in the solvents of Methanol-$d_4$ and DMSO-$d_6$, using a 600-MHz instrument according to a preferred embodiment of the present invention.
Figure 11:
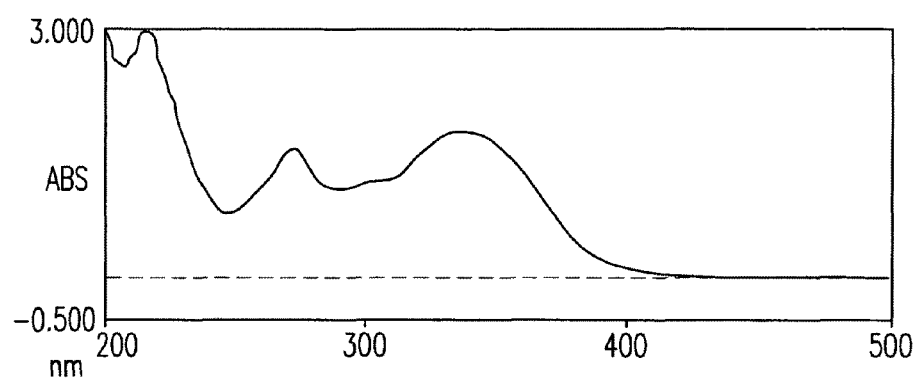
FIG. 11 shows the UV spectrometry of DCMPbL6,7D2H2 according to a preferred embodiment of the present invention.

Furthermore, the purified components DCMPbL6,7D2H2, DCMPbL6,7D3H3, and DCMPbL6,7D4H3 can significantly accelerate the phagocytosis of RPE. For instance, various concentration (0.1, 1, 10, 100 µg/ml) of DCMPbL6,7D2H2 can significantly accelerate the phagocytosis of RPE, and the relevant results are shown in FIG. 4. Please refer to FIG. 4, which is the bar chart illustrating the effects of DCMPbL6,7D2H2 on phagocytosis of RPE. The relevant experimental contents are simply described as follows. $1 \times 10^4$ RPE cells are seeded in 96-well microplate per well, containing 10% FCS in DMEM. After 48 hrs, the medium is changed with 2% FCS in DMEM and then different concentrations of DCMPbL6,7D2H2 are added respectively. After 48 hrs, 50 µl of $2 \times 10^7$ FITC-ROS/ml is added into each well. Four hours later, the unbounded FITC-ROS is washed out with PBS. The fluorescence intensity is detected by a 1420 Multilable counter (PE) measurement system. # $P<0.05$,* $P<0.01$ are obtained by comparing with the phagocytosis of RPE treated with 2% FCS. Although the chemical structure of DCMPbL6,7D2H2 can't be confirmed by the current science yet, the DCMPbL6,7D2H2 is defined by the following NMR spectrums and the UV spectrophotometry. FIGS. 5-10 are the various NMR spectrums of DCMPbL6,7D2H2 in the solvents of Methanol-$d_4$ and DMSO-$d_6$, using a 600-MHz instrument. And, FIG. 11 is the UV spectrometry of DCMPbL6,7D2H2.

Figure 12:
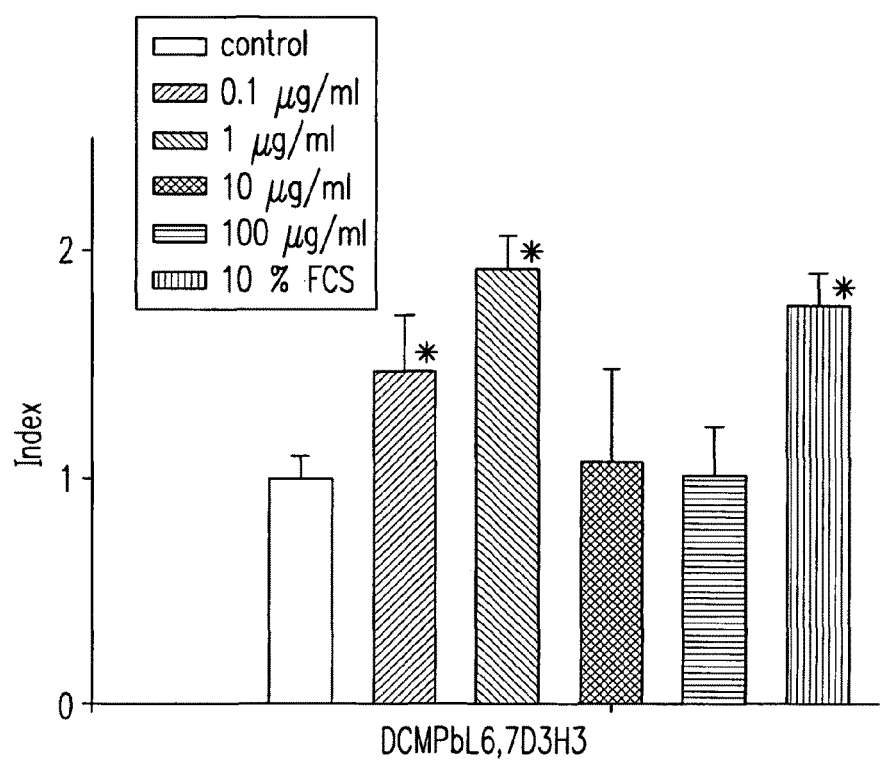
FIG. 12 is the bar chart illustrating the effects of DCMPbL6,7D3H3 on phagocytosis of RPE according to a preferred embodiment of the present invention.
Figure 13:
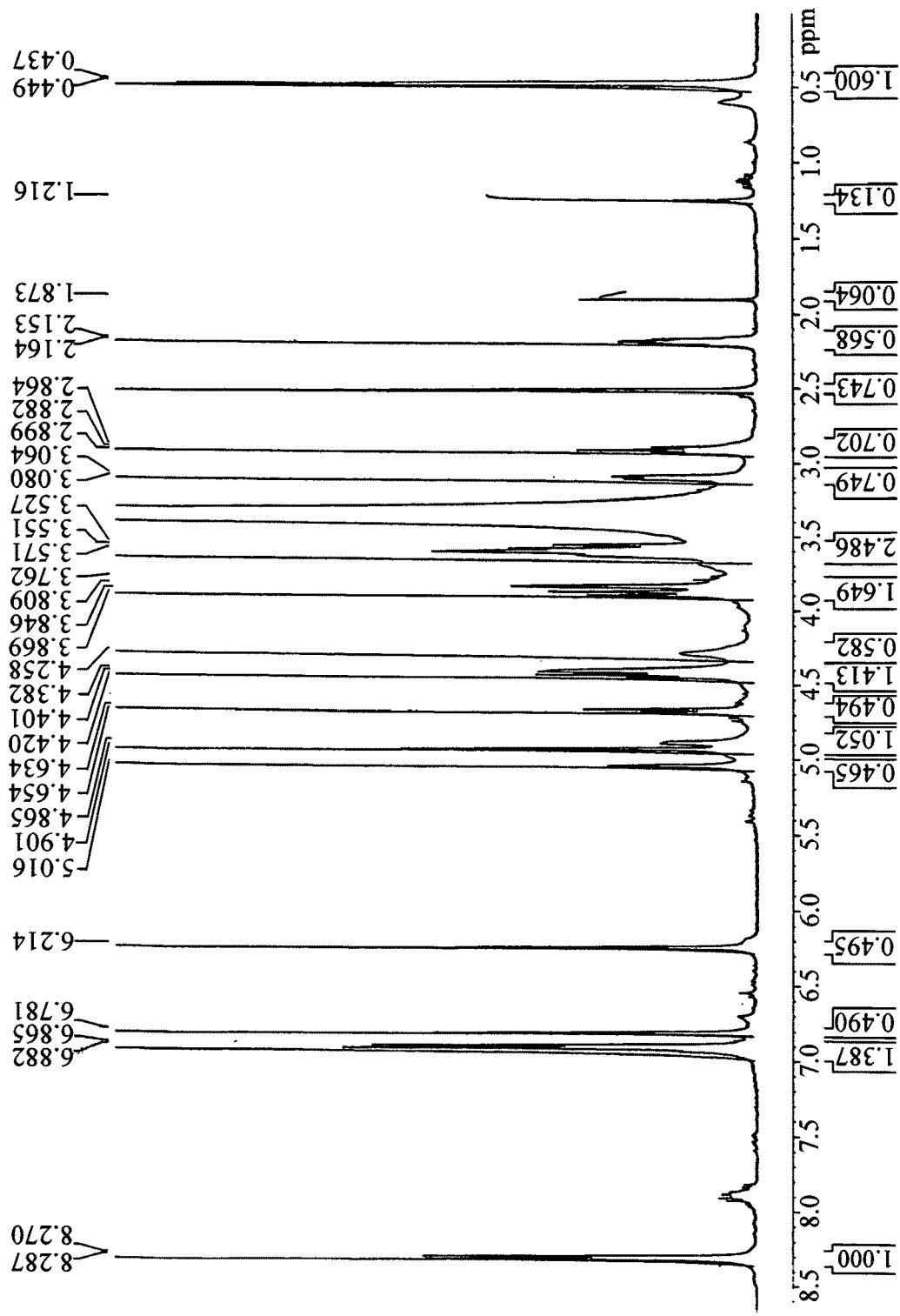
FIG. 13 shows the $^1$H-NMR spectrum of DCMPbL6, 7D3H3 in the solvent of DMSO-$d_6$, using a 500-MHz instrument according to a preferred embodiment of the present invention.
Figure 14:
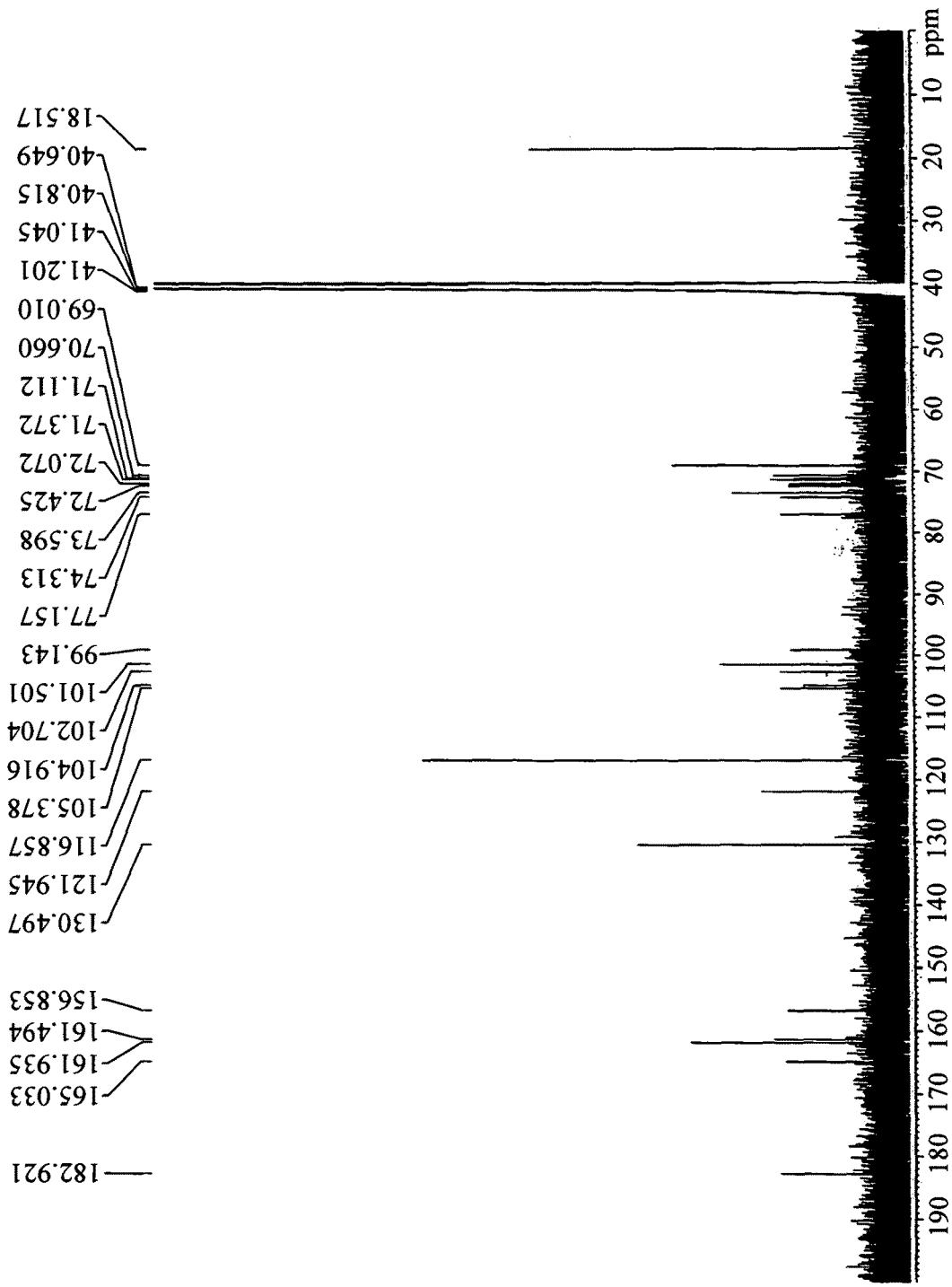
FIG. 14 shows the $^{13}$C-NMR spectrum of DCMPbL6, 7D3H3 in the solvent of DMSO-$d_6$, using a 500-MHz instrument according to a preferred embodiment of the present invention.
Figure 15:
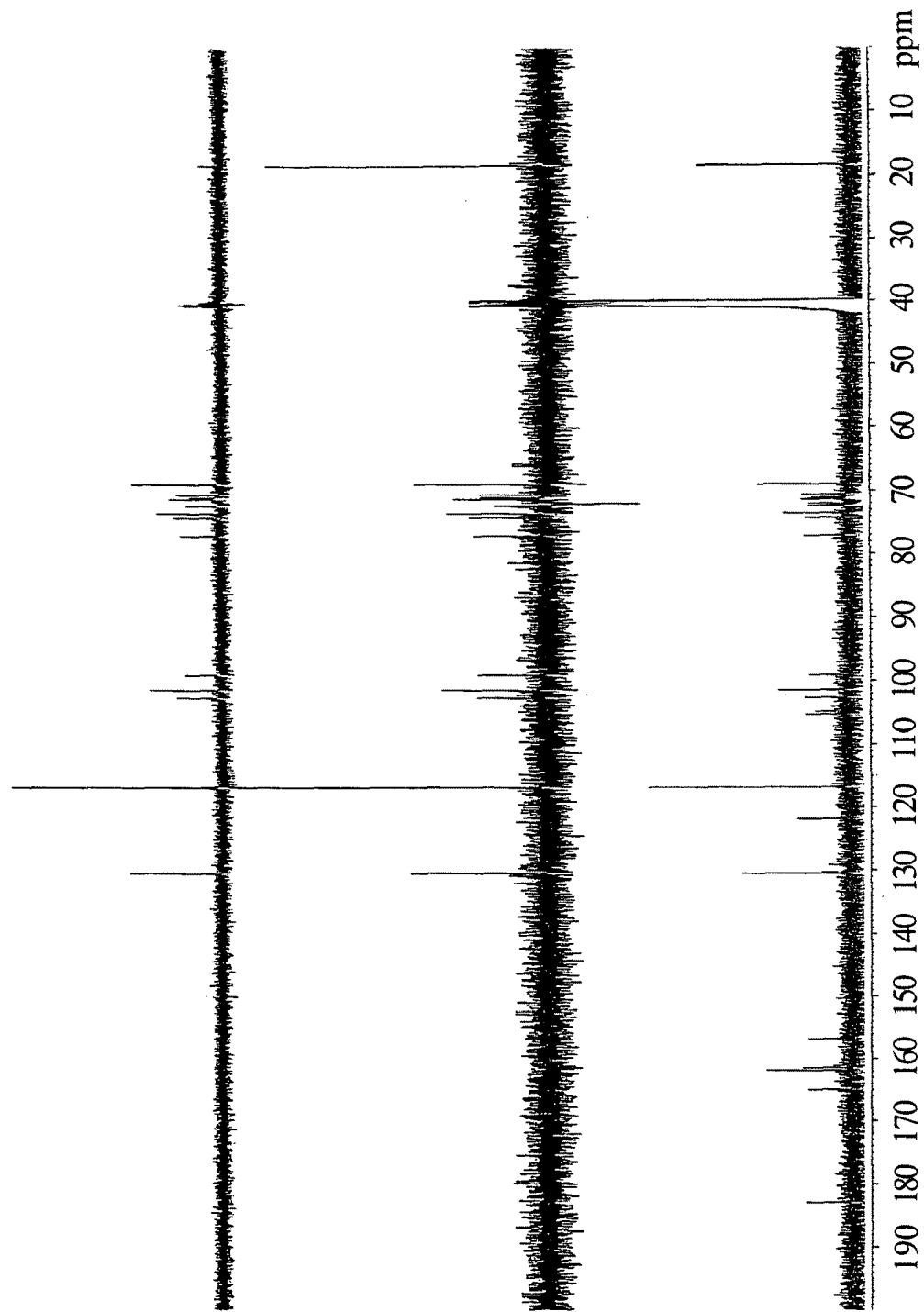
FIG. 15 shows the DEPT spectrum of DCMPbL6,7D3H3 in. the solvent of DMSO-$d_6$, using a 500-MHz instrument according to a preferred embodiment of the present invention.
Figure 16:
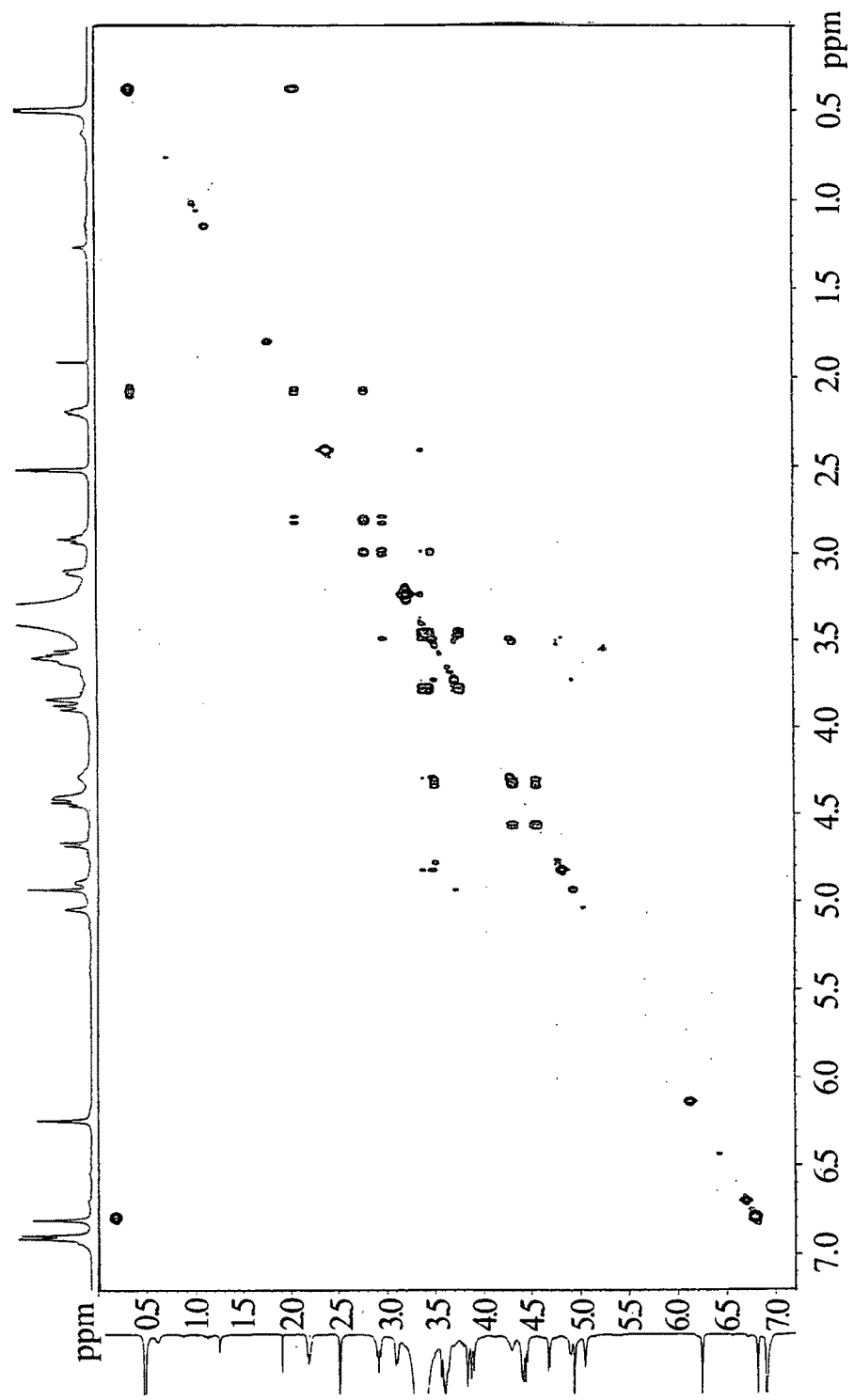
FIG. 16 shows the $^1$H-$^1$H COSY spectrum of DCMPbL6, 7D3H3 in the solvent of DMSO-$d_6$, using a 500-MHz instrument according to a preferred embodiment of the present invention.
Figure 17:
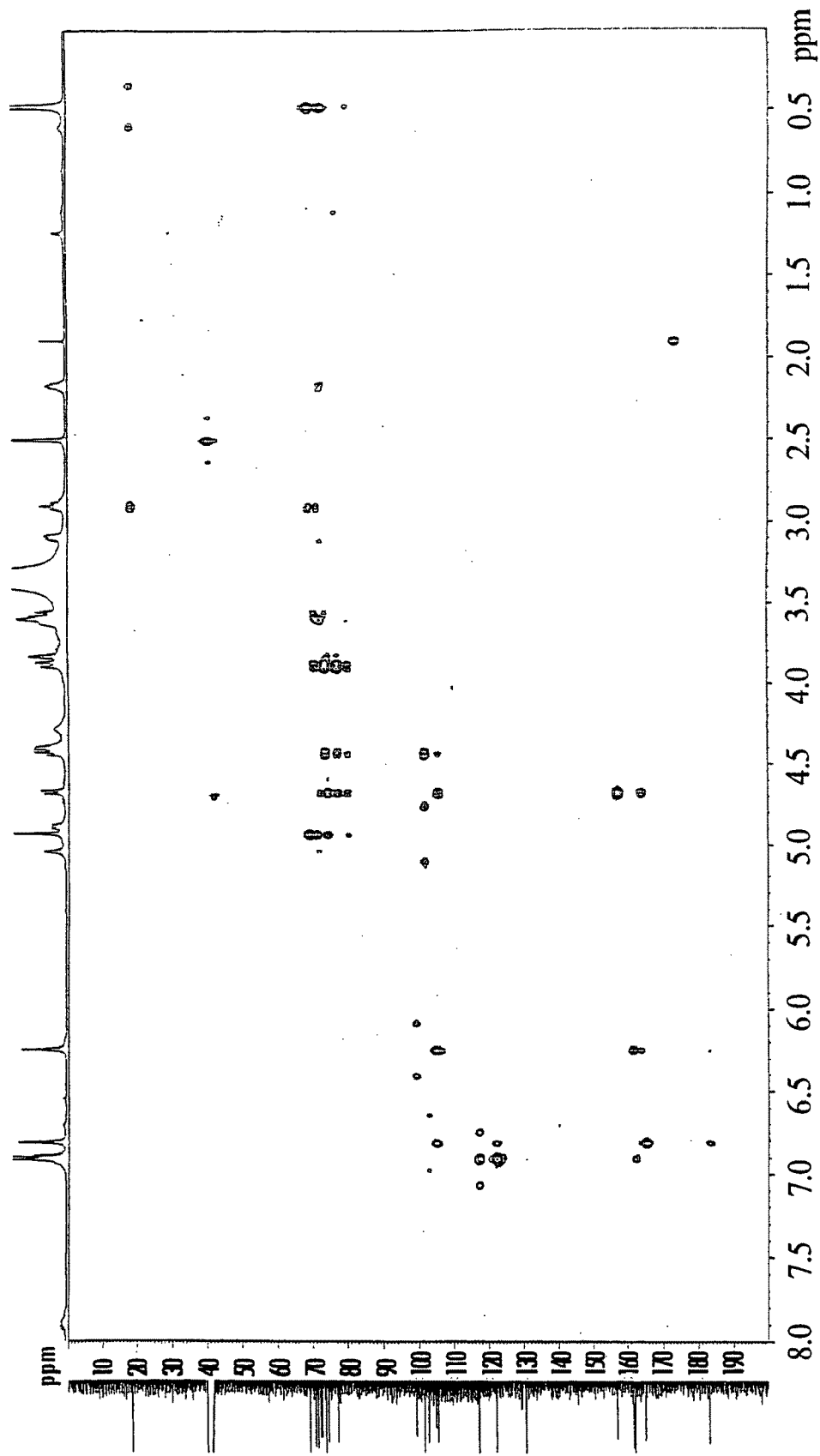
FIG. 17 shows the HMBC spectrum of DCMPbL6,7D3H3 in the solvent of DMSO-$d_6$, using a 500-MHz instrument according to a preferred embodiment of the present invention.

As to the purified component DCMPbL6,7D3H3, various concentration (0.1, 1 µg/ml) of DCMPbL6,7D3H3 can significantly accelerate the phagocytosis of RPE, and the relevant results are shown in FIG. 12. Please refer to FIG. 12, which is the bar chart illustrating the effects of DCMPbL6, 7D3H3 on phagocytosis of RPE. The relevant experimental contents are simply described as follows. $1 \times 10^4$ RPE cells are seeded in 96-well microplate per well, containing 10% FCS in DMEM. After 48 hrs, the medium is changed with 2% FCS in DMEM and then different concentrations of DCMPbL6, 7D3H3 are added respectively. After 48 hrs, 50 µl of $2 \times 10^7$ FITC-ROS/ml is added into each well. Four hours later, the unbounded FITC-ROS is washed out with PBS. The fluorescence intensity is detected by a 1420 Multilable counter (PE) measurement system. * $P<0.01$ is obtained by comparing with the phagocytosis of RPE treated with 2% FCS. Although the chemical structure of DCMPbL6,7D3H3 can't be confirmed by the current science yet, the DCMPbL6,7D3H3 is defined by the following NMR spectrums. FIGS. 13-17 are the various NMR spectrums of DCMPbL6,7D3H3 in the solvent of DMSO-$d_6$, using a 500-MHz instrument.

Figure 18:
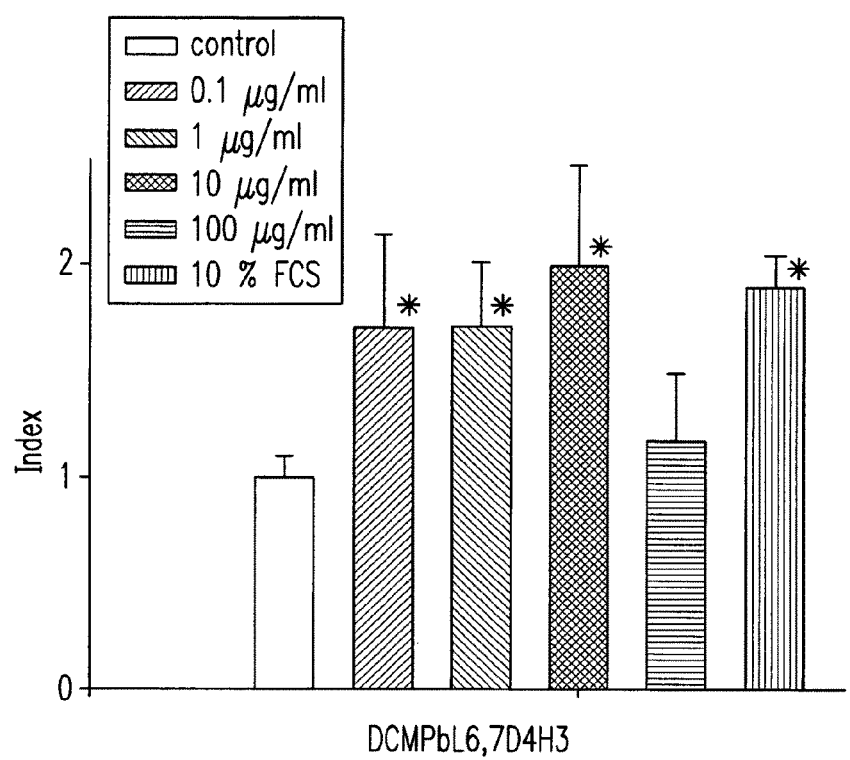
FIG. 18 is the bar chart illustrating the effects of DCMPbL6,7D4H3 on phagocytosis of RPE according to a preferred embodiment of the present invention.
Figure 19:
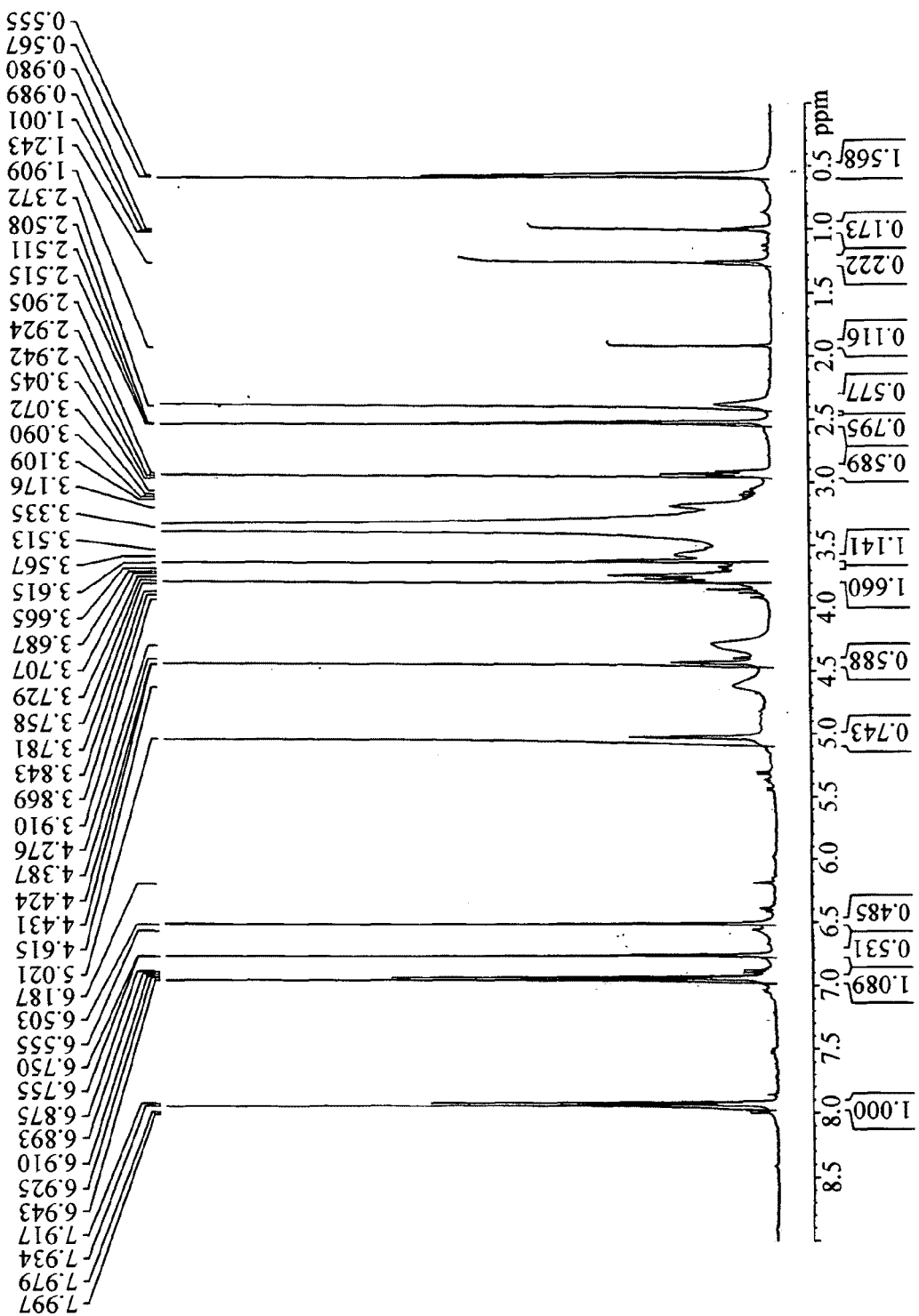
FIG. 19 shows the $^1$H-NMR spectrum of DCMPbL6, 7D4H3 in the solvent of DMSO-$d_6$, using a 500-MHz instrument according to a preferred embodiment of the present invention.
Figure 20:
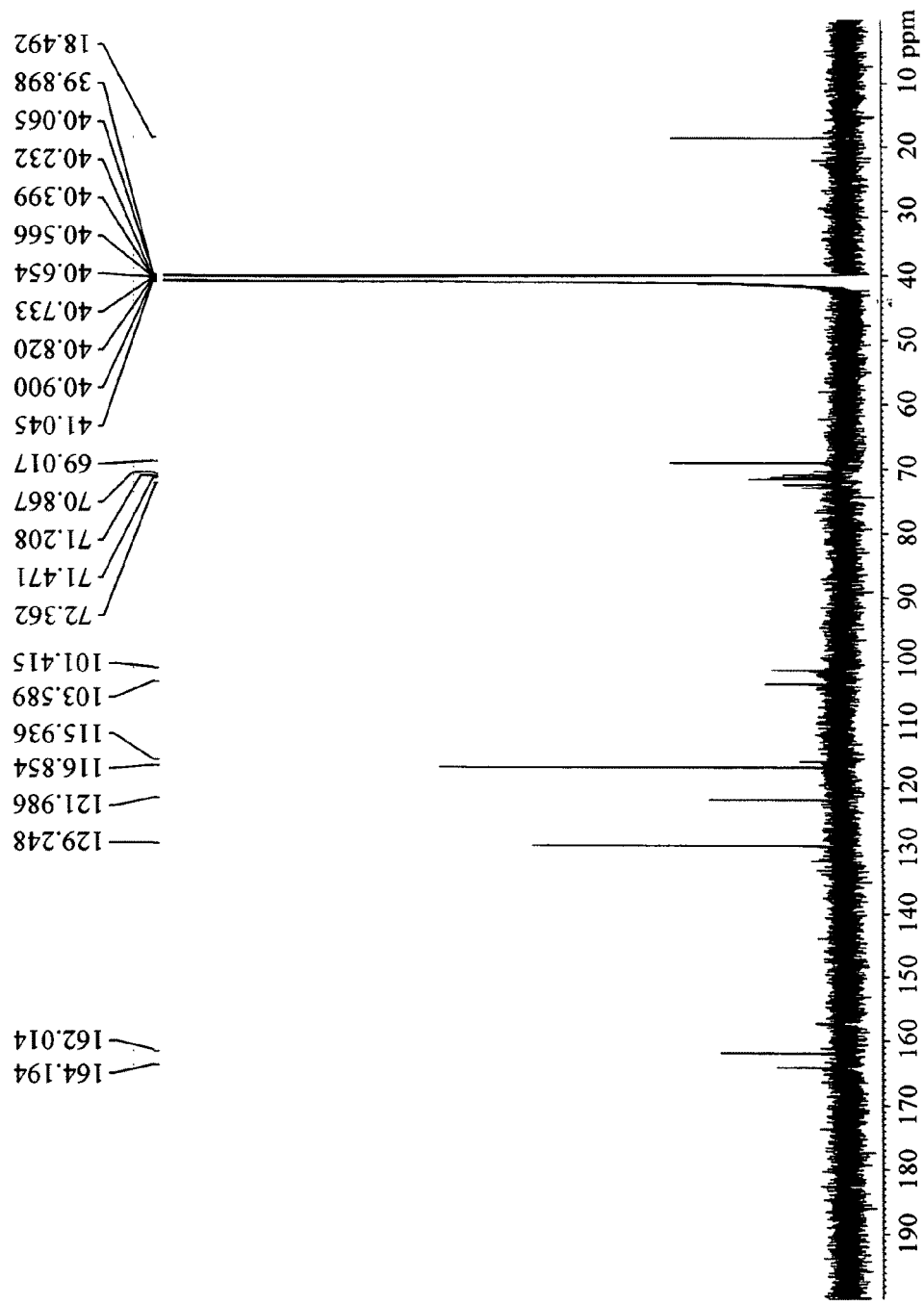
FIG. 20 shows the $^{13}$C-NMR spectrum of DCMPbL6, 7D4H3 in the solvent of DMSO-$d_6$, using a 500-MHz instrument according to a preferred embodiment of the present invention.
Figure 21:
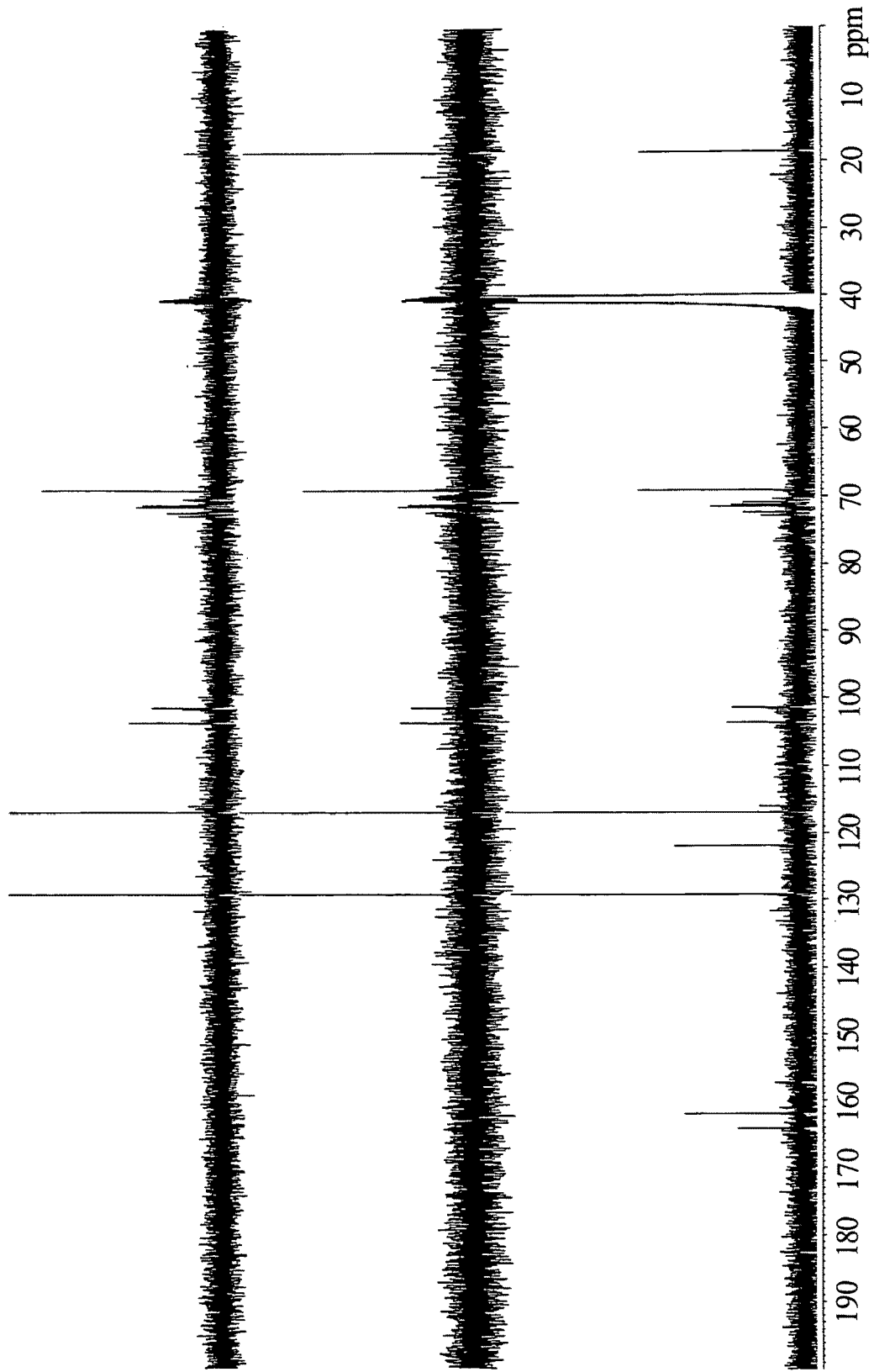
FIG. 21 shows the DEPT spectrum of DCMPbL6,7D4H3 in the solvent of DMSO-$d_6$, using a 500-MHz instrument according to a preferred embodiment of the present invention.
Figure 22:
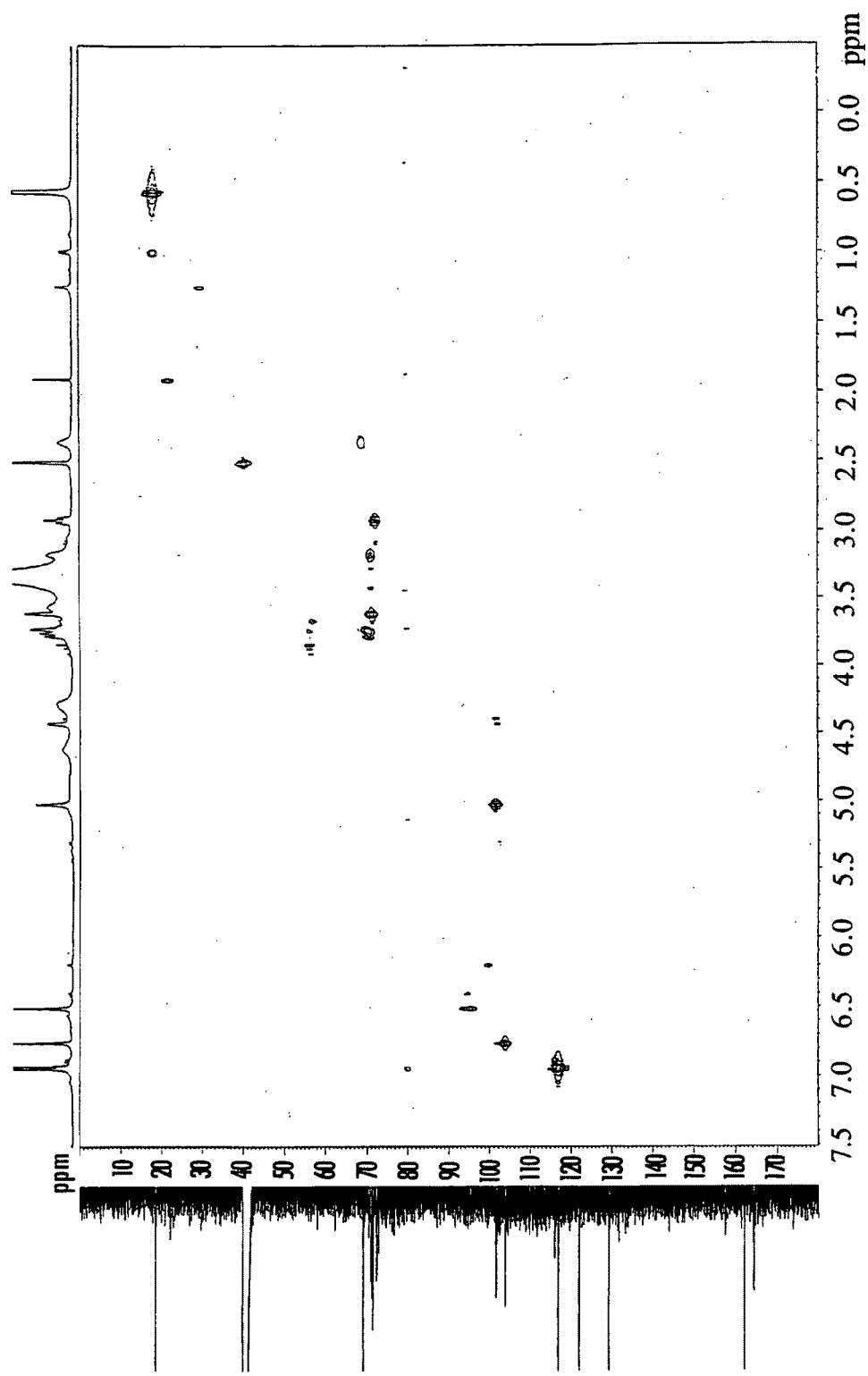
FIG. 22 shows the HMQC spectrum of DCMPbL6,7D4H3 in the solvent of DMSO-$d_6$, using a 500-MHz instrument according to a preferred embodiment of the present invention.
Figure 23:
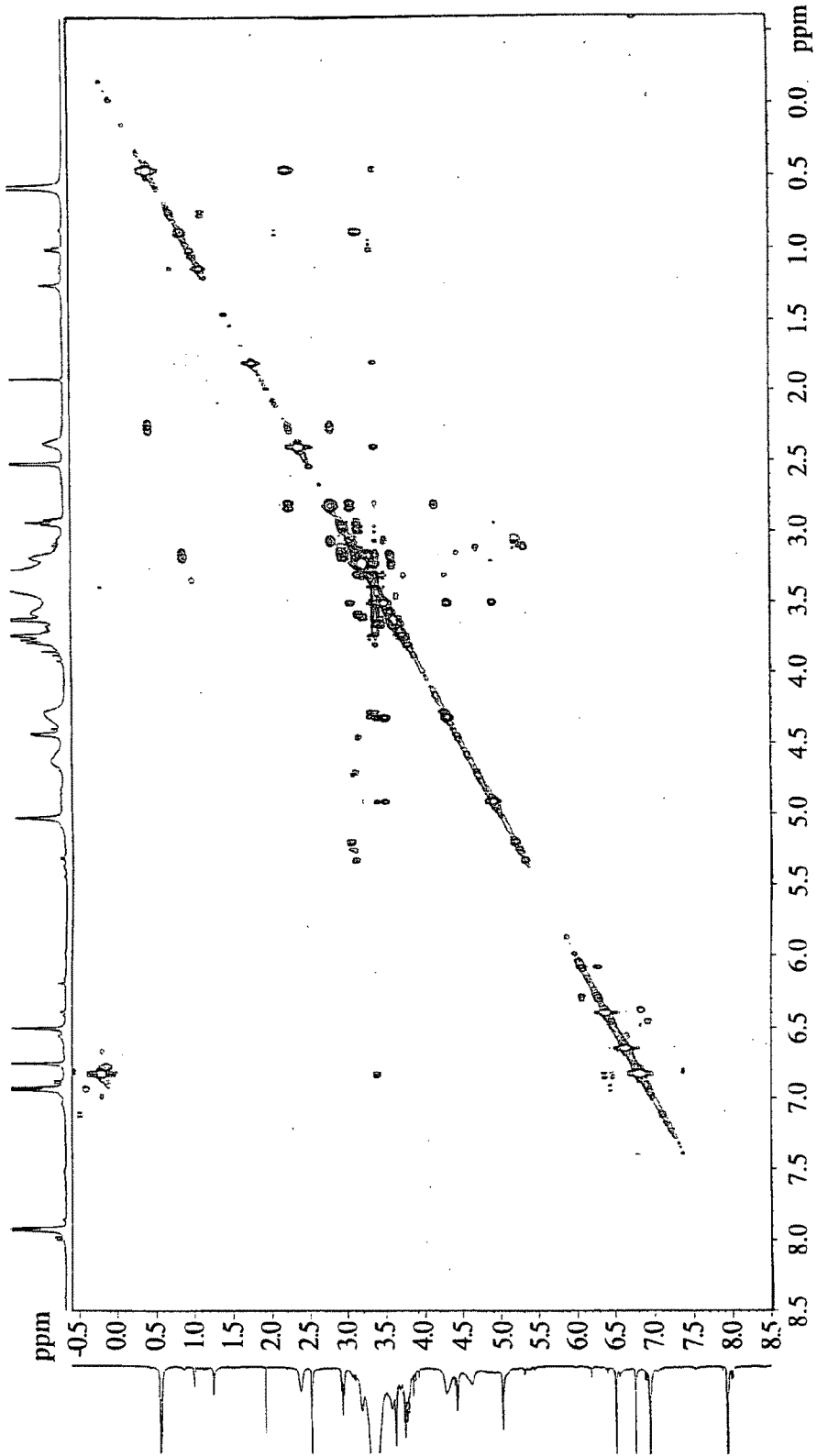
FIG. 23 shows the $^1$H-$^1$H COSY spectrum of DCMPbL6, 7D4H3 in the solvent of DMSO-$d_6$, using a 500-MHz instrument according to a preferred embodiment of the present invention.
Figure 24:
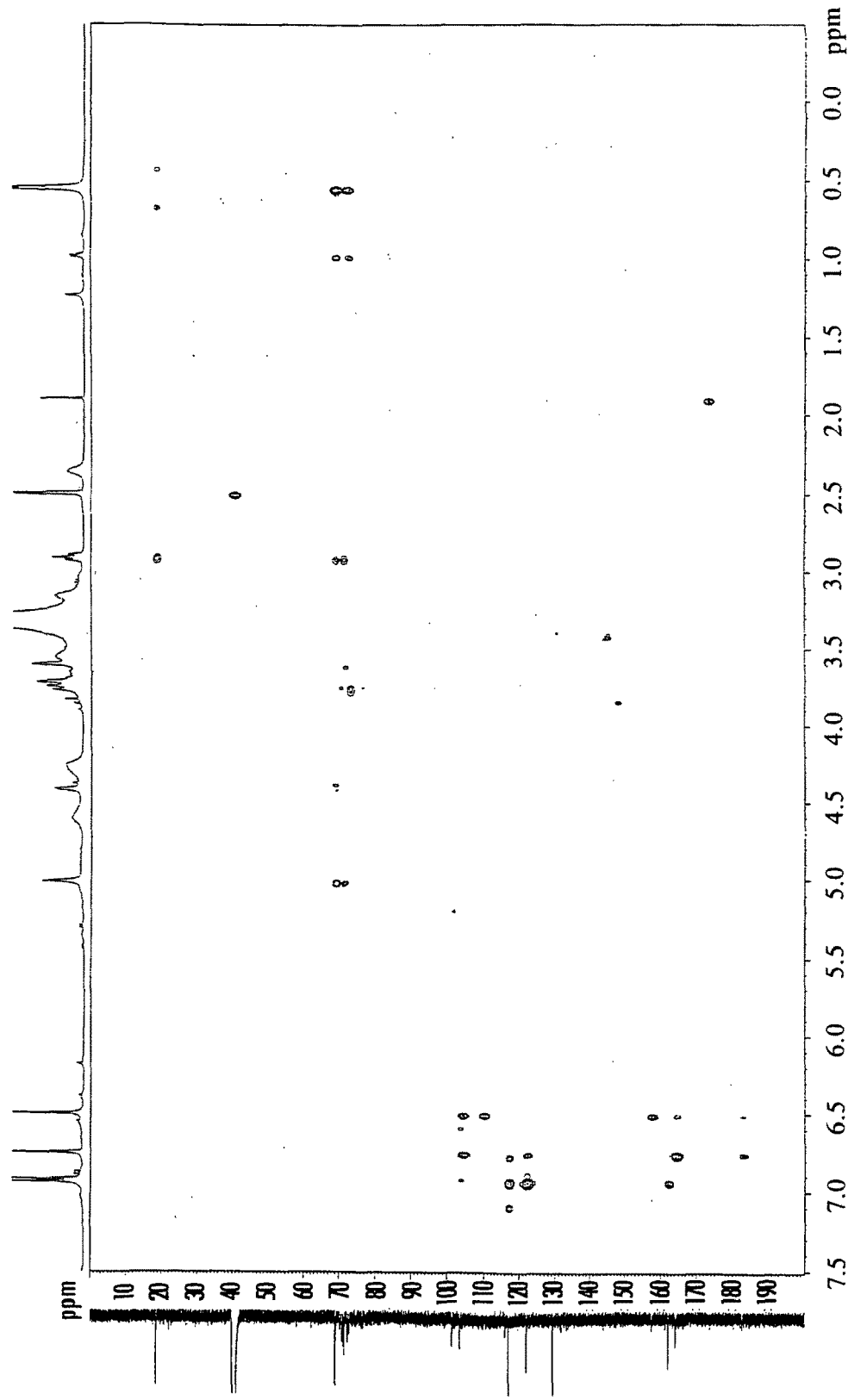
FIG. 24 shows the HMBC spectrum of DCMPbL6,7D4H3 in the solvent of DMSO-$d_6$, using a 500-MHz instrument according to a preferred embodiment of the present invention.

As to the purified component DCMPbL6,7D4H3, various concentration (0.1, 1, 10 µg/ml) of DCMPbL6,7D4H3 can significantly accelerate the phagocytosis of RPE, and the relevant results are shown in FIG. 18. Please refer to FIG. 18, which is the bar chart illustrating the effects of DCMPbL6, 7D4H3 on phagocytosis of RPE. The relevant experimental contents are simply described as follows. $1 \times 10^4$ RPE cells are seeded in 96-well microplate per well, containing 10% FCS in DMEM. After 48 hrs, the medium is changed with 2% FCS in DMEM and then different concentrations of DCMPbL6, 7D4H3 are added respectively. After 48 hrs, 50 µl of $2 \times 10^7$ FITC-ROS/ml is added into each well. Four hours later, the unbounded FITC-ROS is washed out with PBS. The fluorescence intensity is detected by a 1420 Multilable counter (PE) measurement system. * $P<0.01$ is obtained by comparing with the phagocytosis of RPE treated with 2% FCS. Although the chemical structure of DCMPbL6,7D4H3 can't be confirmed by the current science yet, the DCMPbL6,7D3H3 is able to be defined by the following NMR spectrums. FIGS. 19-24 are the various NMR spectrums of DCMPbL6,7D4H3 in the solvent of DMSO-$d_6$, using a 500-MHz instrument.

EXAMPLE XV

Effects of the Extract of *Dendrobii Caicli* on the No Production of RPE.

Figure 25:
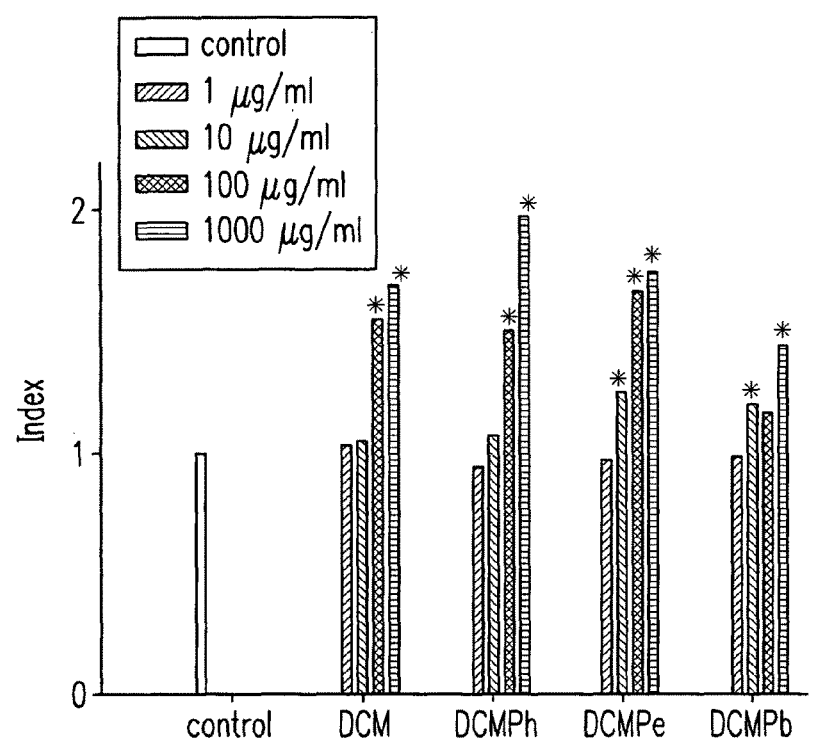
FIG. 25 is the bar chart illustrating the effects of the extract of *Dendrobii Cauli* on nitric oxide (NO) productions of RPE according to a preferred embodiment of the present invention.

Please refer to FIG. 25, which is the bar chart illustrating the effects of the extract of *Dendrobii Cauli* on nitric oxide (NO) productions of RPE. The methanol extract of *Dendrobii Caulis* (DCM) having various concentration (100, or 1000 µg/ml) can significantly accelerate the NO production of RPE, and the relevant results are shown in FIG. 25. The EtOAc extract of *Dendrobii Caulis* (DCMPe) having various concentration (10, or 100, or 1000 µg/ml) can significantly accelerate the NO production of RPE, and the relevant results are shown in FIG. 25. The n-butanol extract of *Dendrobii Caulis* (DCMPe) having various concentration (10, or 1000 µg/ml) can significantly accelerate the NO production of RPE, and the relevant results are shown in FIG. 25. The relevant experimental contents are simply described as follows. $1 \times 10^4$ RPE cells are seeded in 96-well microplate per well, containing 10% FCS in DMEM. After 48 hrs, the medium is changed with 2% FCS in DMEM then different concentrations of the extracts of *Dendrobii Caulis* are added respectively. After 48 hrs, 50 µl of $2 \times 10^7$ FITC-ROS/ml is added into each well. Four hours later, the unbounded FITC-ROS is washed with PBS. The fluorescence intensity is detected by a 1420 Multilable counter (PE) measurement system. * $P<0.05$ is obtained by comparing with the NO production of RPE treated with 2% FCS.

EXAMPLE XVI

Effects of Extracts of *Dendrobii Caulis* on 8-actin and HGF Level in RPE Cell Lysates.

Figure 26:
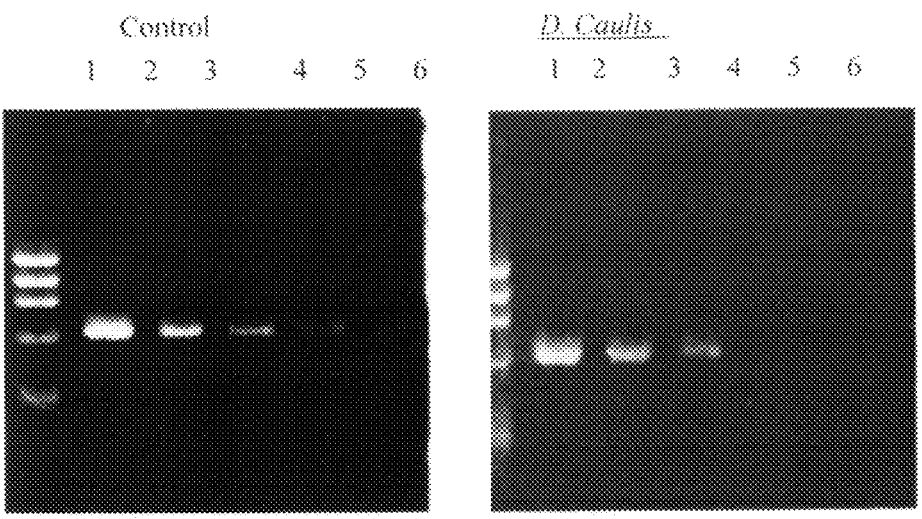
FIGS. 26 (A)-(B) show the electrophoresis results showing the effect of the extracts of *Dendrobii Caulis* on β-action (A), and HGF (B) levels in RPE according to a preferred embodiment of the present invention.
Figure 26:
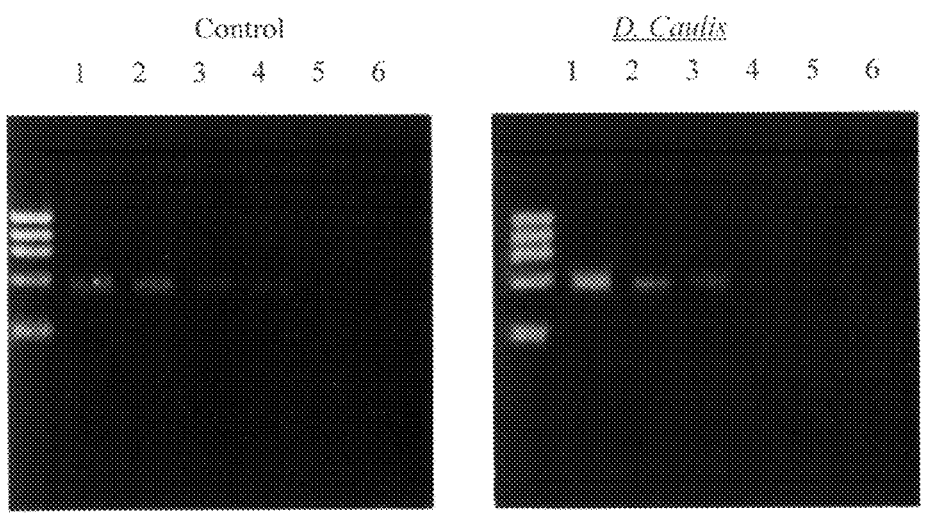

Please refer to FIGS. 26 (A)-(B), which are the electrophoresis results of showing the effect the extracts of *Dendrobii Caadis* on β-action (A), and HGF (B) levels in RPE cell. The expression level is shown by cDNA quantity, in which the cDNA is obtained from RPE cell lysates via RT-PCR steps. The relevant experimental contents are simply described as follows. Confluenced RPE cells are shifted to DMEM with 2% FCS and 1000 µg/ml of extracts of *Dendrobii Caulis* for 24 hrs. cDNA is generated from 1 µg total RNA as a template (1×). Lane 1: φ X174/Hae III marker, Lane 2: 1× template, Lane 3: 2× dilution of template, Lane 4: 4× dilution of template, Lane 5 8× dilution of template, Lane 6 16× dilution of template. As shown in FIG. 26, the methanol extract of *Dendrobii Caulis* (DCM) can significantly accelerate the expression of HGF, since the RPE cells treated with the extracts of *Dendrobii Caulis* have stronger HGF cDNA expression level.

Figure 27:
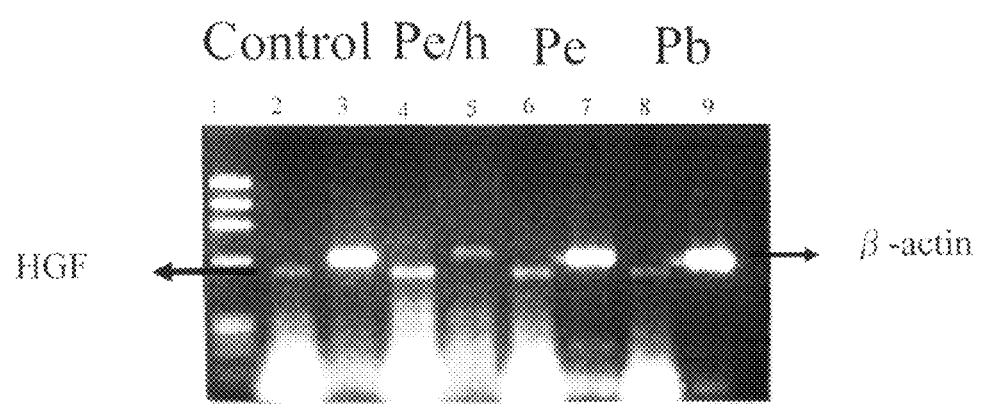
FIG. 27 shows the electrophoresis diagram showing the effect of the chemical solvent partition extracts of *Dendrobii Caulis* on HGF mRNA expression of RPE according to a preferred embodiment of the present invention.

Please refer to FIG. 27, which is the electrophoresis diagram showing the effect of the chemical solvent partition extracts of *Dendrobii Caulis* on HGF mRNA expression of RPE. The experimental steps are similar to that of FIG. 2b. As shown in FIG. 27, the n-hexane extract of *Dendrobii Caulis* (Ph) can significantly accelerate the expression of HGF, since the RPE cells treated with Ph clearly shows a stronger HGF cDNA expression level.

EXAMPLE XVII

Effects of extracts of *Dendrobii Caulis* on bFGF, VEGF, and TGF-β Inhibitions of a Normal RPE and a Hypoxia RPE.

Figure 28:
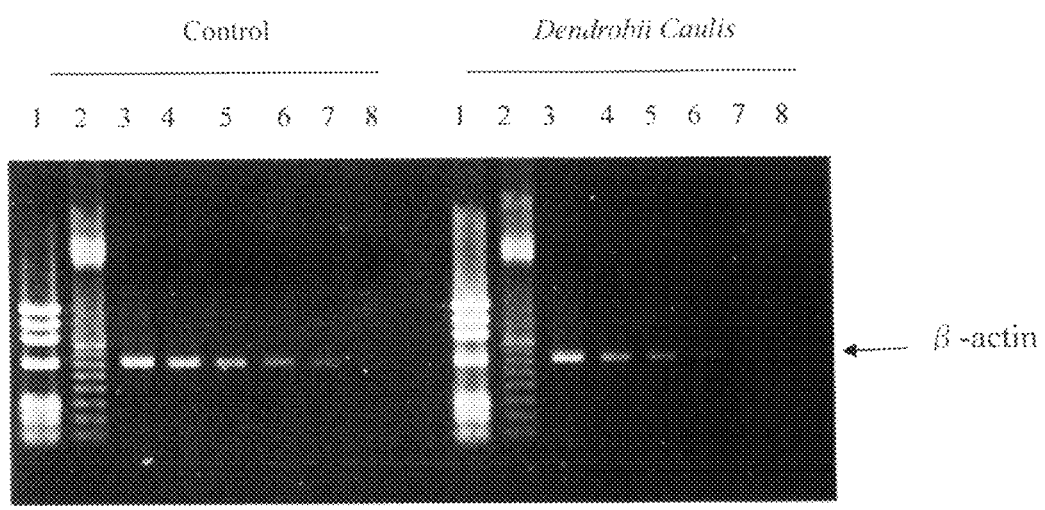
FIGS. 28 (A) to (B) show the electrophoresis results of the effect of the extracts of *Dendrobii Caulis* on the expressions of β-actin, and bFGF for normal RPE according to a preferred embodiment of the present invention.
Figure 28:
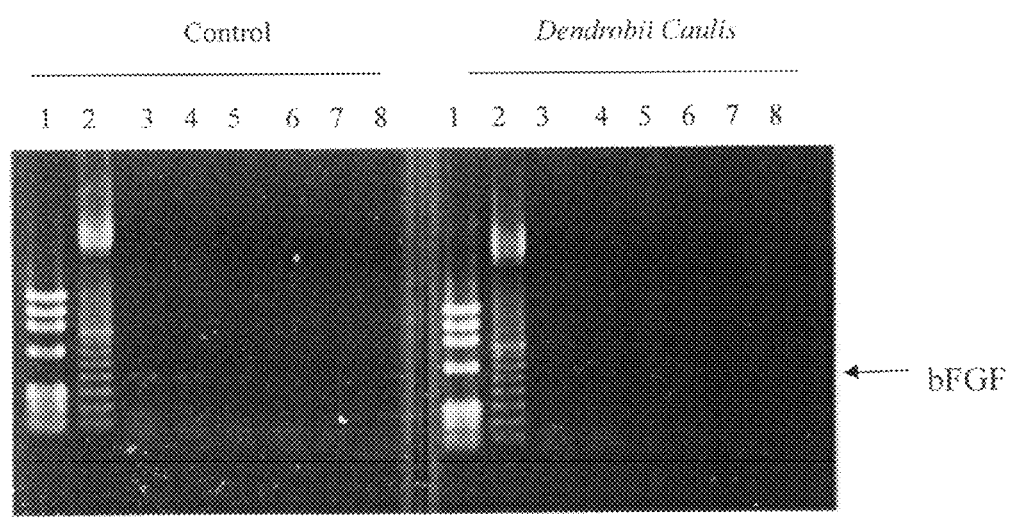
Figure 29:
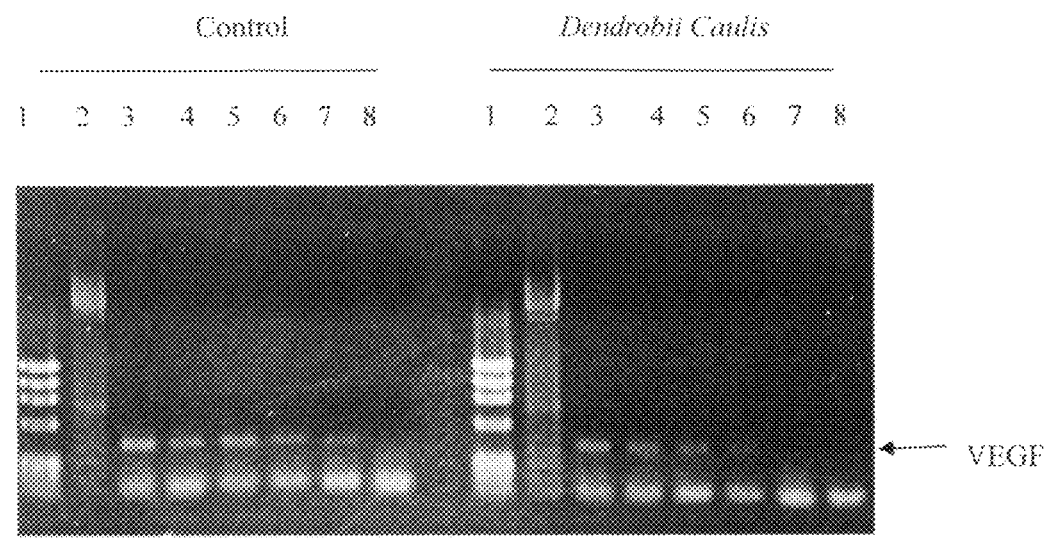
FIGS. 29 (A) to (B) show the indirectly relevant results of the effect of the extracts of *Dendrobii Caulis* on the expressions of VEGF, and TGF-β for normal RPE according to a preferred embodiment of the present invention.
Figure 29:
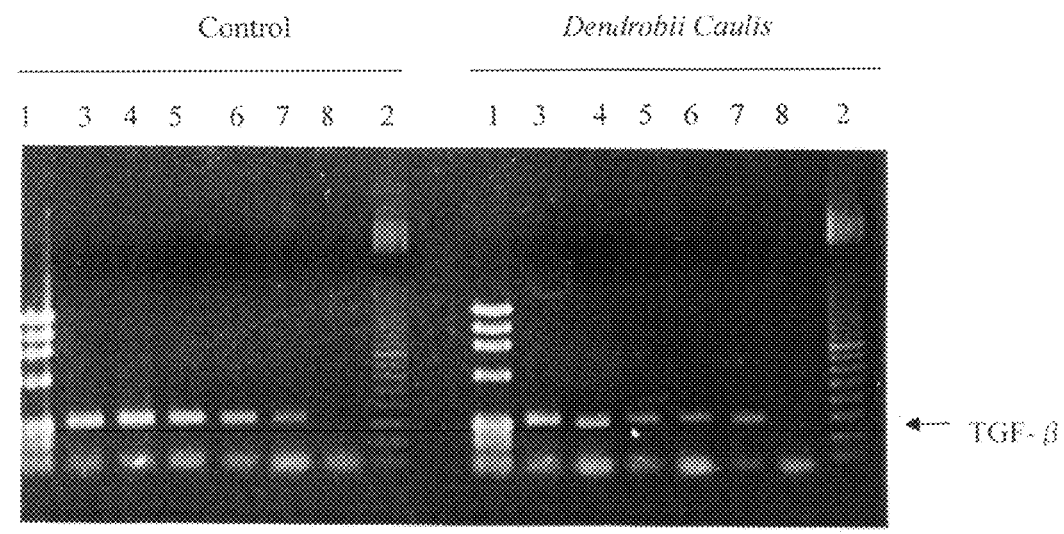

The extracts of *Dendrobii Caulis* having an effective concentration are added into RPE. After incubated for 48 hrs, the RNA is extracted from the cell lysate, and then the template cDNA is formed from the RNA by RT-PCR. The concentration of the template cDNA is two times and the following results are indirectly quantitated according to this concentration. Please refer to FIGS. 28 (A) to 29 (B), which are the relevant results of the extracts of Dendrobii Caulis on the expressions of β-actin, bFGF, VEGF, and TGF-β for normal RPE. In which, the result of α-actin is a control set. FIGS. 28 (A) and (B) are the electrophoresis results of the effect of the extracts of *Dendrobii Caulis* on the expressions of (A) β-actin and (B) bFGF. The cDNA generated from the mRNA of the normal RPE by using 1 µg of total RNA as a template (1×). The results shown in pictures descriptions are: Lane 1: φX174 marker, Lane 2: 100 bp ladder marker, Lane 3: 1× template, Lane 4: 2× dilution of template, Lane 5: 4× dilution of template, Lane 6: 8× dilution of template, Lane 7: 16× dilution of template, and Lane 8: 32× dilution of template. FIGS. 29 (A) and (B) are the electrophoresis result of the effect of the extracts of *Dendrobii Caulis* on the expressions of VEGF (A) and TGF-β (B). The cDNA is generated from the mRNA of the normal RPE by using 1 µg of total RNA as a template (1×). The relevant results shown in pictures are: Lane 1: φ X174 marker, Lane 2: 100 bp ladder marker, Lane 3: 1× template, Lane 4: 2× dilution of template, Lane 5: 4× dilution of template, Lane 6: 8× dilution of template, Lane 7: 16× dilution of template, and Lane 8: 32× dilution of template. As shown in FIGS. 28-29, for a normal RPE, the extracts of *Dendrobii*

*Caulis* inhibit the expression of the bFGF mRNA to 25% and the expression of the VEGF mRNA to 50%. However, the extracts of *Dendrobii Caulis* have no influence on the expression of the TGF-β mRNA.

Figure 30:
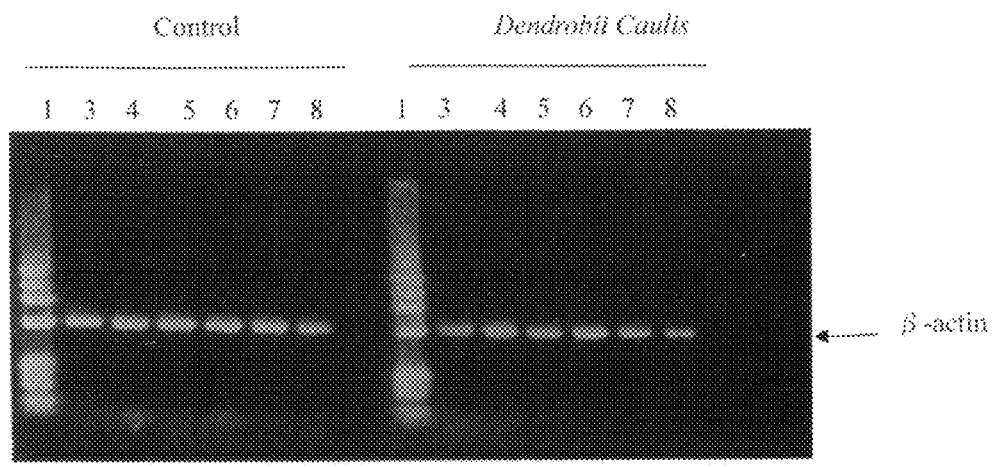
FIGS. 30 (A) to (B) show the indirectly relevant results of the effect of the extracts of *Dendrobii Caulis* on the expressions of β-actin, and bFGF for hypoxia RPE according to a preferred embodiment of the present invention.
Figure 30:
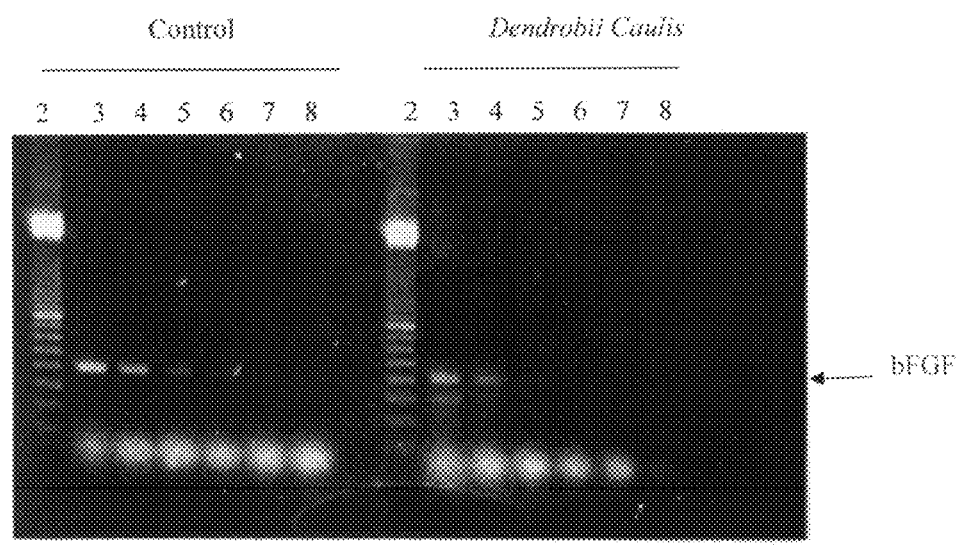
Figure 31:
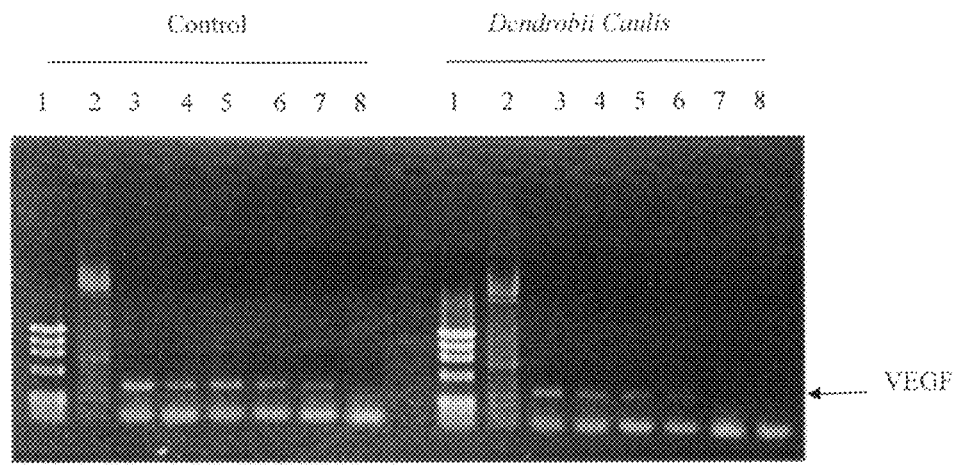
FIGS. 31 (A) to (B) show the indirectly relevant results of the effect of the extracts of *Dendrobii Caulis* on the expressions of VEGF, and TGF-β for hypoxia RPE according to a preferred embodiment of the present invention.
Figure 31:
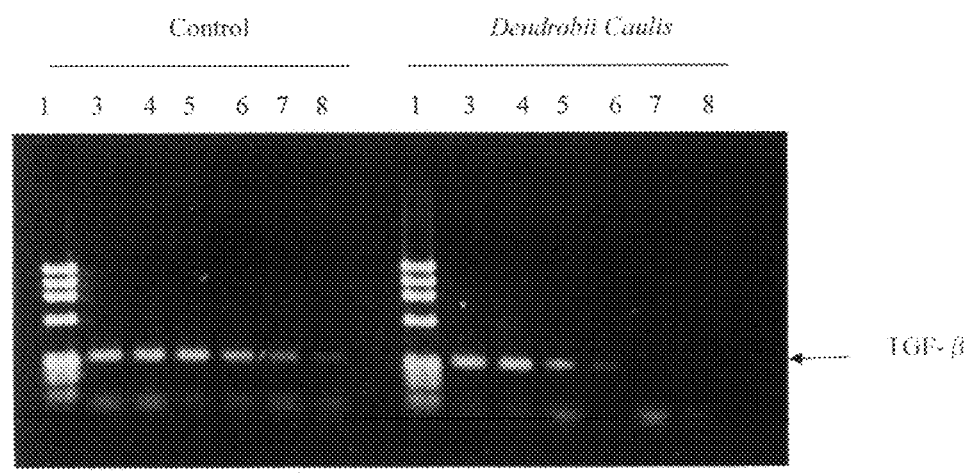

Please refer to FIGS. 30 (A) to 31 (B), which are the electrophoresis results of the effects of the extracts of *Dendrobii Caulis* on the expressions of β-actin, bFGF, VEGF, and TGF-β for hypoxia RPE. In which, the results of β-actin are control set. FIGS. 30 (A) and (B) are the electrophoresis result of the extracts of effect of the *Dendrobii Caulis* on the expressions of (A) β-actin and (B) bFGF. The cDNA is generated from the mRNA of the hypoxia RPE by using 1 μg of total RNA as a template (1×). The relevant results shown in pictures are: Lane 1: φ X174 marker, Lane 2: 100 bp ladder marker, Lane 3: 1× template, Lane 4: 2× dilution of template, Lane 5: 4× dilution of template, Lane 6: 8× dilution of template, Lane 7: 16× dilution of template, and Lane 8: 32× dilution of template. FIGS. 31 (A) and (B) are the electrophoresis results of the extracts of the effect of *Dendrobii Caulis* on the expressions of VEGF (A) and TGF-β (B). The cDNA is generated from the mRNA of the hypoxia RPE by using 1 μg of total RNA as a template (1×). The relevant results shown in pictures are: Lane 1: φ X174 marker, Lane 2: 100 bp ladder marker, Lane 3: 1× template, Lane 4: 2× dilution of template, Lane 5: 4× dilution of template, Lane 6: 8× dilution of template, Lane 7: 16× dilution of template, and Lane 8: 32× dilution of template. As shown in FIGS. 30-31, for a hypoxia RPE, the extracts of *Dendrobii Caulis* inhibit the expression of the bFGF mRNA to 50%, the expression of the VEGF mRNA to 50%, and the expression of the TGF-β mRNA to 25%. Obviously, the extracts of *Dendrobii Caulis* have different inhibitory effects on the growth factors when the RPE cells are under normal or hypoxia environment. In other words, the extracts of *Dendrobii Caulis* selectively regulate the expressions of the genes, such as bFGF, VEGF, TGF-β, which all play important roles in the ophthalmic defects.

EXAMPLE XVIII

Preparation of AGE-BSA in vitro A BSA (bovine serum albumin, fraction V) solution having the concentration of 0.1 g/ml is prepared by dissolving appropriate amount of BSA into 1×PBS solution. A glucose solution having the concentration of 180 mg/ml glucose is prepared by dissolving appropriate amount of glucose into a 1×PBS solution. After being filtered through the aseptic 0.22 μm membrane, 5 ml of the BSA solution and 5 ml of the glucose solution are both added into a 15 ml test tube, while the reaction concentrations for BSA and glucose are respectively 760 mM and 0.5 M. Then, the reaction solution is sealed up and incubated in the incubator in the dark at 37° C. And, the control experiment is prepared without adding glucose. After incubated for 2, 4, 8, 12, 16 weeks, the reaction solution is dialyzed four times with the de-ionized water having a volume of 100 times of the reaction solution for removing the glucose. Then, the obtained solution is filtered under an aseptic condition, lyophilized, and weighted for determining the contents and redissolved. After being respectively aliquoted and lyophilized, the aliquoted reaction solution is stored at −20° C.

EXAMPLE XIX

The Change of AGE-BSA Degradation Ability of the RPE Cell Treated with the Extracts of *Dendrobii Caulis* and HGF.

1×10⁶ RPE cells are seeded into the 96-well microplate, containing 10% FCS in DMEM, at 37° C., supplied with 5% $CO_2$. After incubation of 48 hrs, five sets of experiment are respectively treated with the *Dendrobii Caulis* crude extract and HGF, in which each set of experiment includes two microplates for different treating time. After treating for 36 or 48 hrs, 0.01% EDTA is added into the microplate for harvesting the cells, and then the cells are suspended in the DMEM and the cell number is counted. Then, the cell solution is centrifuged for 5 min at 1200 rpm, and the cells are suspended back into 10 ml DEME twice. Then, the cell solution is centrifuged again, and is suspended back again in the 0.7 ml Homogenization buffer (50 mM sodium acetate buffer, pH4.5, 1 mM DTT, 0.15M NaCl, 3 mM NaND containing 0.1% TritonX-100. Then, the cell solution is vibrated by a sonicator for 15 sec, four cycles, so as to break the cell completely. Next, the cell solution is centrifuged at 13000 rpm for 15 mins, vibrated by a sonicator for 15 sec, four cycles, and centrifuged again at 11000 rpm for 15 min. The supernatant is then collected and filtrated under an aseptic condition. The protein concentration is detected. 1000 μg/ml AGE-BSA are filtrated under an aseptic condition. After reacting for 0, 6, 12, 24, 48, 72 hrs, the corresponding electrophoresis is proceeded in order to observe the conformation and the degree of the AGE-BSA degradation.

EXAMPLE XX

Effects of the Methanol Extracts of *Dendrobii Caulis* (Dcm) and Hepatocyte Growth Factor on the RPE Cell Proteolysis Activity.

After being treated with the methanol extracts of *Dendiobii Caulis* (DCM) or HGF and incubated for 36 hrs, the extracted cellular extracts will be proceeded with the following experiments with all fractions. The cellular extracts are reacted with AGE-BSA by adding AGE-BSA having the same amount as that of the cellular extracts. That's to say, the ratio of the enzyme to the substrate is 1:1, and both concentrations of the cellular extracts and the AGE-BSA are controlled at 500 μg/ml. It's known that the proteolysis activities of different treatments are not obviously different (not shown), and the reaction rates are relatively high during the incubation period of 12 to 48 hrs. Further, the proteolysis activities of different treatments are a little bit different (not shown) during the incubation period of 48 to 72 hrs.

Figure 32:
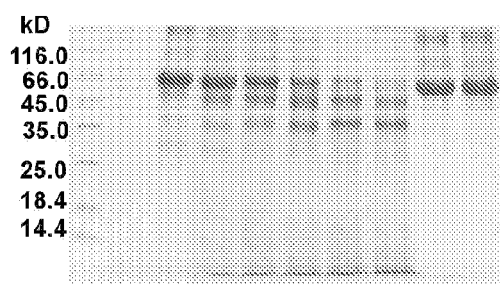
FIG. 32 (A)-(E) show the electrophoresis results of the proteolytic activity of cultured RPE after being treated with DCM or HGF according to a preferred embodiment of the present invention.
Figure 32:
Figure 32:
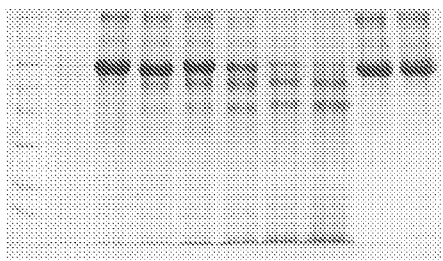
Figure 32:
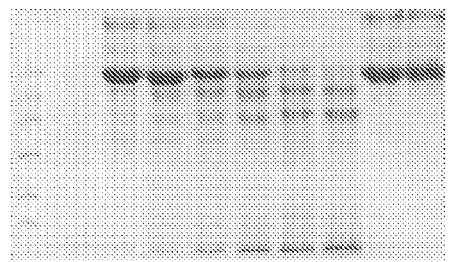
Figure 32:
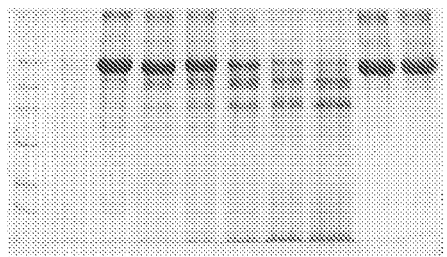
Figure 33:
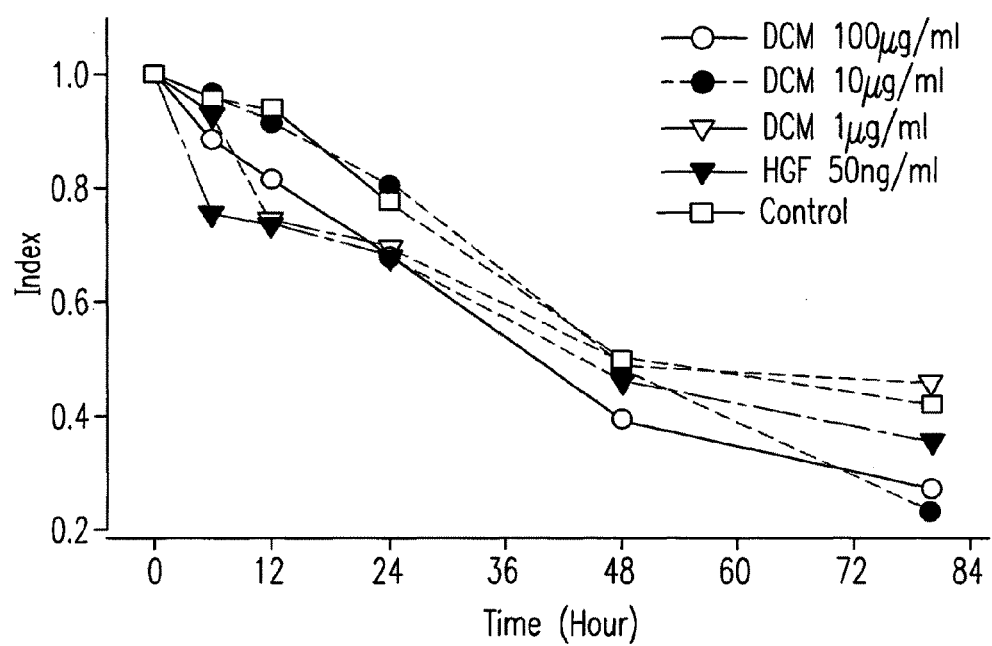
FIG. 33 shows the relevant results of the proteolytic activity of cultured RPE after being treated with DCM or HGF according to a preferred embodiment of the present invention.

Please refer to FIG. 32. FIG. 32 shows the electrophoresis results of the effects of DCM or HGF for the proteolytic activities of the cultured RPE cell. The activities are assayed by different incubation time with AGE-BSA. The different symbols represent different treatments: (a) DCM 100 μg/ml, (b) DCM 10 μg/ml, (c) DCM 1 μg/ml, (d) 50 ng/ml HGF and (e) without treated DCM or HGF as control. RPE cells (1×10⁶ cells/petri dish) are cultured in DMEM with 10% FCS for 48 hr. After reaching 90% confluence, RPE cells are incubated with various concentrations of DCM in 2% FCS or 50 ng/ml HGF for 48 hours. Cellular extracts (shown as lane 2 on each gel) were incubated with AGE for 0 to 82 hours (from lane 3 to lane 8). And, AGE is incubated alone as negative control (lane 9, 10). In addition, please refer to FIG. 33. FIG. 33 shows the proteolytic activity of cultured RPE cell after being treated with DCM or HGF. In which, the proteolytic activity on each time point is showed as index comparing with the start time of incubation. The mount of residual BSA or AGE-BSA are quantitated by ImageQuant software and drawn as degradation curve. As FIG. 32 shows, the proteolytic activities caused by treating with 10 μg/ml DCM and 50 ng/ml HGF are a little bit greater than that of the control set. And, as shown in FIG. 33, the amount of AGE-BSA will be obviously decreased by being treated with 10 μg/ml DCM, 100 μg/ml DCM, and 50 ng/ml HGF. In which, the influence of 10 μg/ml DCM is the greatest. Therefore, it's known that proper amount of DCM or HGF will have influence on the proteolytic activity of the RPE cell.

EXAMPLE XXI

Effects of Extracts of *Dendrobii Caulis* on the Advanced Glycated Endproduct Concentration in Sera of Streptozotocin Induced Diabetic Mice.

C57BL/6J male mice, aged 6 weeks, are continuously treated with the Streptozotocin (STZ) at the dose of 50 mg/kg/day by injecting 0.15 M citric acid buffer, pH 4.5, IP for five days. After further 12 to 14 days, the blood sugars of the mice are tested by the orbital blood sampling method. The mice with blood sugar concentration higher than 250 mg/dl are collected, and then are divided into four sets for the following experiments. The four sets of mice are respectively fed with the forage containing various amount of the methanol extract of *Dendrobii Caulis*, 0 mg/kg/day, 20 mg/kg/day, 100 mg/kg/day, and 500 mg/kg/day. Then, the blood sugars of the mice are sampled and tested once per week. If the blood sugars of the mice are decreased, the mice needed to be injected with STZ 200 mg/kg/day for keeping the blood sugars of the mice high. After 4 to 8 weeks, the sera of the mice are sampled and the blood sugars and AGE AB contained therein are tested. Further, the eyes, liver, and the kidney of the mice are sampled and treated with HE stain, and then treated with paraffin to form paraffin embedding sections. The weights of the mice, and the consumptions of water and forage are recorded during the experiment. And, the appearance of the fur and the circulations of limbs and the tail are observed and photographed for recording.

Figure 34:
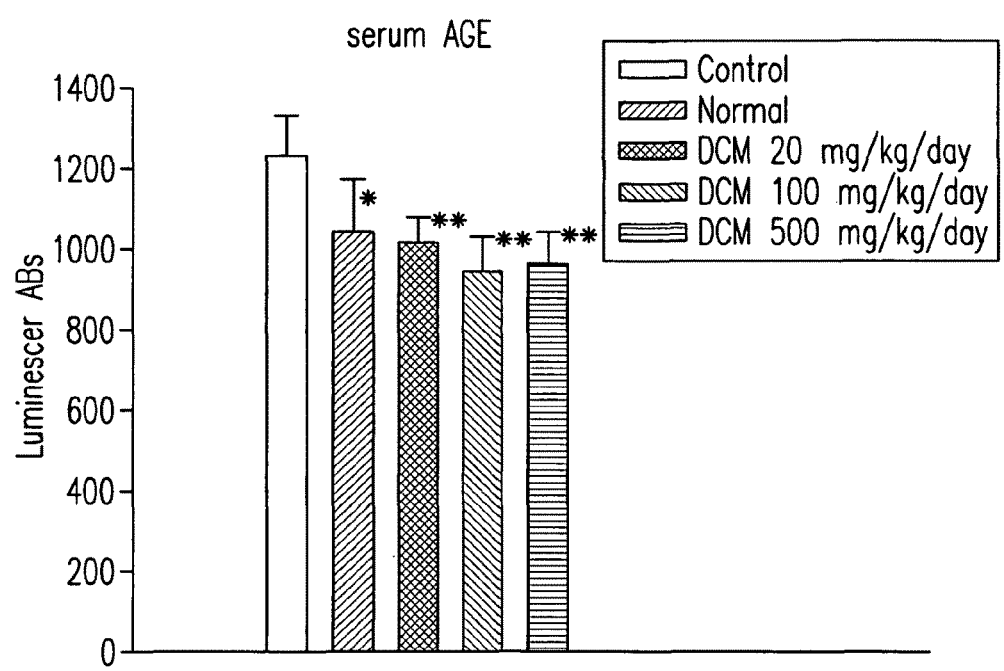
FIG. 34 shows the relevant results of the effects of the extracts of *Dendrobii Caulis* on the advanced glycated end-products concentration in sera of streptozotocin induced diabetic mice according to a preferred embodiment of the present invention.

Please refer to FIG. 34. FIG. 34 shows the advanced glycated endproduct concentrations in sera of the Streptozotocin (STZ) induced diabetic mice. In which, the sera are respectively obtained from diabetic mice and the age-matched control mice, 10 weeks after the STZ administration. Values are respective the means STD of 5 independent experiments (*P, 0.05, ** p<0.001 vs the control group). The relevant results show that the methanol extract of *Dendrobii Caulis* can significantly increase the AGE degradation in the Streptozotocin (STD) induced diabetic mice. Therefore, it appears that the methanol extracts of *Dendrobii Caulis* is curative for the diabetic complication induced by AGE.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for treating a retinal pigment epithelium (RPE) cell-related disorder comprising:
   administering to a mammal an extract of a plant *Dendrobii Caulis*, which is obtained by an extraction of said plant or parts thereof with a water miscible organic solvent or a mixture of the water miscible organic solvent with water.

2. The method as claimed in claim 1, wherein said organic solvent is one selected from a group consisting of an alcohol having 1 to 8 carbon atoms, an alkane, and an ester.

3. The method as claimed in claim 2, wherein said alcohol is one of methanol and ethanol.

4. The method as claimed in claim 1, wherein said extract of said plant *Dendrobii Caulis* is a physiological active fraction of a pharmaceutical composition.

5. The method as claimed in claim 4, wherein said pharmaceutical composition comprises a physiologically acceptable carrier being a pharmaceutical carrier.

6. The method as claimed in claim 1, wherein the RPE cell-related disorder is at least one of an age related macular degeneration and a diabetic retinopathy.

* * * * *

```
SEQUENCE LISTING

<160> NUMBER OF SEQ ID NOS: 14

<210> SEQ ID NO 1
<211> LENGTH: 1804
<212> TYPE: DNA
<213> ORGANISM: Bos taurus

<400> SEQUENCE: 1
ccacgcgtcc gcgccggtcg acaccgcaac cagttcgcca tggatgatga tattgctgcg      60
ctcgtggtcg acaacggctc cggcatgtgc aaggccggct tcgcgggcga cgatgctccc     120
cgggccgtct tcccgtccat cgtggggcgc ccccggcacc agggcgtaat ggtgggcatg     180
ggccagaagg actcgtacgt gggggatgag gctcagagca agagaggcat cctgacccta     240
aagtacccca ttgagcacgg catcgtcacc aactgggacg acatggagaa gatctggcac     300 cacccttct acaacgagct ccgtgtggcc cctgaggagc accccgtgct gctgaccgag     360 gccccctga accccaaggc caaccgtgag aagatgaccc agatcatgtt cgagaccttc     420 aacaccctg ccawgtacgt ggccatccag gctgtgctgt ccctgtatgc ctctggccgc     480
accaccggca tcgtgatgga ctccggtgac ggggtcaccc acacggtgcc catctatgag     540
gggtacgccc ttcccatgc catcctgcgt ctggacctgg ctggccggga cctgacggac     600
tacctcatga agatcctcac ggagcgtggc tacagcttca ccaccacggg ccgagcggaa     660
atcgtccgtg acatcaagga gaagctctgc tacgtggccc tggacttcga gcaggagatg     720
gccaccgcgg cctccagctc ctccctggas aasagctacg agcttcctga cgggcaggtc     780
atcaccatcg gcaatgagcg gttccgctgc cctgaggctc tcttccagcc ttccttcctg     840
ggcatggaat cctgcggcat tcacgaaact accttcaatt tcatcatgaa gtgtgacgtc     900
gacatccgca aggacctcta cgccaacacg gtgctgtccg gcgggaccac catgtaccc     960 ggcatcgcgg acaggatgca gaaagagatc actgccctgg cacccagcac aatgaagatc    1020
```

```
aagatcatcg cgcccctga gcgcaagtac tccgtgtgga ttggcggctc catcctggcc    1080
tcgctgtcca ccttccagca gatgtggatc agcaagcagg agtacgatga gtccggcccc    1140
tccatcgtcc accgcaaatg cttctaggcg gactgttagc tgcgttacac ccttttttctt   1200 gacaaaacct aacttgcgca gaaaacgaga tgagattggc atggctttat ttgtttttt    1260 ttttgtcttt tttgatttt ttttttttt ggcgcttgac tcaggattta aaaactggaa    1320
cggtgaaggt gacagcagtc ggttggatcg agcattccca aagttctaca gtgtggccga    1380
ggacttgatt gtacatggtt ttgtttttt tttaatagtc attccaaata tcgcgaaatg    1440
cattgttaca ggaagtcctt tgccttccca aaagccaccc cgcttctctc taaggagaag    1500
gggccagtcc tcgcccgagt ccacacaggg gaggtgatcg cttttgtgta aattatgtac    1560
tccaaaacaa attttgtttt taatcttcgc cttaatactt gtttttttttg tttgttttat    1620 tttgaatgga cagccatcat ggacccctt ttttgtccct caacttgaga tgtatgaagg    1680
cttttggtcc cctgggagc gggttgaggt gcggaggcag tcagggcttt cctgtacact    1740
gacttgagac cagttcaata aagtgcacac cttaaaaaaa aaaaaaaaaa aaaaaaaaa    1800 aaaa                                                               1804

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggattctca gtatcctcac a                                             21

<210> SEQ ID NO 3
<211> LENGTH: 2492
<212> TYPE: DNA
<213> ORGANISM: Bos taurus

<400> SEQUENCE: 3
cacacaacaa acttagctca tcgcaataaa aagcagctca gagccgacgg gctcttttag     60
gctctgagtc ggaagagggt tctttcaccc aggcatctgc tccagtggga tccgccagca    120
cacccagcag gaccatgtgg gtgaccagac ttctgccagt cctgctgctg cagcacgtcc    180
tcctccacct cctcctgctt cccatcgcca tcccctatgc agaaggacag aagaaaagaa    240
gaaacacact tcatgaattc aaaaggtcag caaagactac tctaattaaa gaggacccat    300
tactgaagat aaaaacaaaa aaaatgaaca ctgcagacca atgtgccaat agatgtatta    360
ggaataaagg acttccattc acttgcaagg cctttgtttt tgataaagca agaaaacgat    420
gcctctggtt ccctttcaat agcatgtcaa gtggagtaaa aaaagagttt ggccatgaat    480
ttgacctcta tgaaaacaaa gactacatta gaaactgtat cattggtaaa ggcggtagct    540
acaaggggac ggtatctatc actaaaagtg gcatcaaatg tcagccctgg aattccatga    600
taccacacga acacagcttt ttgccttcga gctatcgggg taaagaccta caggaaaact    660
actgtcgaaa tcctcgaggg gaagaagggg gaccttggtg tttcacaagc aatccagagg    720
tacgctacga agtctgtgac attcctcagt gttcagaagt tgaatgcatg acctgcaatg    780
gggaaagtta ccgaggtccc atggatcaca cagaaacagg caagatttgt cagcgctggg    840
atcatcagac accacaccgg cacaaattct tgccagaaag atatcctgac aagggctttg    900
```

```
                                      -continued
atgataatta ttgccgcaat cctgatggca agccgaggcc atggtgctat actcttgacc    960
ctgacacccc ctgggagtac tgtgcaatta aaatgtgcgc ccacagtact atgaatgaca    1020
cagatctccc tatgcaaacg actgaatgca ttcaaggtca aggagaaggt taccggggca    1080
ccatcaatac catttggaat ggaattccct gtcagcgttg ggattcccag tatcctcacc    1140
agcatgacat aactcctgaa aatttcaagt gcaaggacct aagagaaaat tattgccgaa    1200
atccagatgg ggctgagtca ccgtggtgtt ttaccactga tccaaacatc cgagttggct    1260
actgctccca aattccaaaa tgtgacgtgt caagtggaca agattgttat cgtgggaatg    1320
gcaaaaacta tgggcagt ttatccaaaa cacgatctgg actaacatgt tcgatgtggg     1380
ataagaacat ggaagattta caccggcata tcttctggga accagatgct actaagctga    1440
ataagaatta ctgtcggaat cctgatgacg atgcccacgg tccctggtgt tacacaggga    1500
atcctctcat tccttgggat tattgcccta tttctcgttg tgagggcgat accacaccta    1560
caatagtcaa tttagaccat ccagtaatat cttgcgccaa acaaaacag ttgcgagttg      1620 taaatggaat tccaacacga acaaatgtag gatggatggt tagttttgaaa tacagaaata   1680 aacatatctg cggaggatca ttgataaagg aaagttggat tcttactgca agacagtgtt    1740
tcccttctcg aaacaaggac ttgaaagatt atgaagcttg gcttggaatt catgatgtcc    1800
atgggagagg agatgagaaa cgcaaacagg ttctaaatgt tacccaactg gtatatgggc    1860
ctgaaggatc agatctggta ttactgaagc ttgctaggcc tgctattttg gatgattttg     1920
ttagtacaat tgatttacct aattatgggt gcacaattcc tgagaaaacc acttgcagtg    1980
tttatggctg gggctacact ggattgatca actcagatgg tctactacga gtagcacatc    2040
tctatattat ggggaatgag aaatgcagcc aatatcatca agggaaggtg actctgaatg    2100
agtctgaaat atgtgctggg gctgaaaata ttgtatcagg accatgtgag ggagattatg    2160
gtggcccact tgtttgtgaa caacataaaa tgagaatggt tcttggtgtc attgttcctg    2220
gtcgtggctg tgccattcca aaccgtcctg gtatttttgt ccgagtggca tattatgcaa    2280
aatggataca caaaatcata ttaacgtata aggcaccaca gttgtagctg gtataactgt    2340
ctgaagcttc caataacaca agtctctttt acatgaagat tttggagtac atggaattaa    2400
aatgtaactt aaaaatcctg agacaactac ttgagtgtca tgtttgttaa gatactcatt    2460
aatatttatg ggtgttttct gttgttttgt tg                                    2492

<210> SEQ ID NO 4
<211> LENGTH: 730
<212> TYPE: PRT
<213> ORGANISM: Bos taurus

<400> SEQUENCE: 4

Met Trp Val Thr Arg Leu Leu Pro Val Leu Leu Gln His Val Leu
  1               5                  10                  15

Leu His Leu Leu Leu Leu Pro Ile Ala Ile Pro Tyr Ala Glu Gly Gln
                 20                  25                  30

Lys Lys Arg Arg Asn Thr Leu His Glu Phe Lys Arg Ser Ala Lys Thr
         35                  40                  45

Thr Leu Ile Lys Glu Asp Pro Leu Leu Lys Ile Lys Thr Lys Met
     50                  55                  60

Asn Thr Ala Asp Gln Cys Ala Asn Arg Cys Ile Arg Asn Lys Gly Leu
 65                  70                  75                  80

Pro Phe Thr Cys Lys Ala Phe Val Phe Asp Lys Ala Arg Lys Arg Cys
                 85                  90                  95
```

```
Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
            115                 120                 125

Ile Ile Gly Lys Gly Gly Ser Tyr Lys Gly Thr Val Ser Ile Thr Lys
            130                 135                 140

Ser Gly Ile Lys Cys Gln Pro Trp Asn Ser Met Ile Pro His Glu His
145                 150                 155                 160

Ser Phe Leu Pro Ser Ser Tyr Arg Gly Lys Asp Leu Gln Glu Asn Tyr
                    165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
                    195                 200                 205

Val Glu Cys Met Thr Cys Asn Gly Glu Ser Tyr Arg Gly Pro Met Asp
210                 215                 220

His Thr Glu Thr Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                    245                 250                 255

Asp Asn Tyr Cys Arg Asn Pro Asp Gly Lys Pro Arg Pro Trp Cys Tyr
                260                 265                 270

Thr Leu Asp Pro Asp Thr Pro Trp Glu Tyr Cys Ala Ile Lys Met Cys
            275                 280                 285

Ala His Ser Thr Met Asn Asp Thr Asp Leu Pro Met Gln Thr Thr Glu
290                 295                 300

Cys Ile Gln Gly Gln Gly Glu Gly Tyr Arg Gly Thr Ile Asn Thr Ile
305                 310                 315                 320

Trp Asn Gly Ile Pro Cys Gln Arg Trp Asp Ser Gln Tyr Pro His Gln
                325                 330                 335

His Asp Ile Thr Pro Glu Asn Phe Lys Cys Lys Asp Leu Arg Glu Asn
            340                 345                 350

Tyr Cys Arg Asn Pro Asp Gly Ala Glu Ser Pro Trp Cys Phe Thr Thr
            355                 360                 365

Asp Pro Asn Ile Arg Val Gly Tyr Cys Ser Gln Ile Pro Lys Cys Asp
            370                 375                 380

Val Ser Ser Gly Gln Asp Cys Tyr Arg Gly Asn Gly Lys Asn Tyr Met
385                 390                 395                 400

Gly Ser Leu Ser Lys Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Thr Lys Leu Asn Lys Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Val Gly Trp Met Val Ser Leu Lys
            500                 505                 510

Tyr Arg Asn Lys His Ile Cys Gly Gly Ser Leu Ile Lys Glu Ser Trp
            515                 520                 525
```

```
Ile Leu Thr Ala Arg Gln Cys Phe Pro Ser Arg Asn Lys Asp Leu Lys
    530                 535                 540

Asp Tyr Glu Ala Trp Leu Gly Ile His Asp Val His Gly Arg Gly Asp
545                 550                 555                 560

Glu Lys Arg Lys Gln Val Leu Asn Val Thr Gln Leu Val Tyr Gly Pro
                565                 570                 575

Glu Gly Ser Asp Leu Val Leu Leu Lys Leu Ala Arg Pro Ala Ile Leu
            580                 585                 590

Asp Asp Phe Val Ser Thr Ile Asp Leu Pro Asn Tyr Gly Cys Thr Ile
        595                 600                 605

Pro Glu Lys Thr Thr Cys Ser Val Tyr Gly Trp Gly Tyr Thr Gly Leu
    610                 615                 620

Ile Asn Ser Asp Gly Leu Leu Arg Val Ala His Leu Tyr Ile Met Gly
625                 630                 635                 640

Asn Glu Lys Cys Ser Gln Tyr His Gln Gly Lys Val Thr Leu Asn Glu
                645                 650                 655

Ser Glu Ile Cys Ala Gly Ala Glu Asn Ile Val Ser Gly Pro Cys Glu
            660                 665                 670

Gly Asp Tyr Gly Gly Pro Leu Val Cys Glu Gln His Lys Met Arg Met
        675                 680                 685

Val Leu Gly Val Ile Val Pro Gly Arg Gly Cys Ala Ile Pro Asn Arg
    690                 695                 700

Pro Gly Ile Phe Val Arg Val Ala Tyr Tyr Ala Lys Trp Ile His Lys
705                 710                 715                 720

Ile Ile Leu Thr Tyr Lys Ala Pro Gln Leu
                725                 730

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agaaacccca cgaagtggtg aagt                                           24

<210> SEQ ID NO 6
<211> LENGTH: 1536
<212> TYPE: DNA
<213> ORGANISM: Bos taurus

<400> SEQUENCE: 6
cagcgctgac ggacagacag acagacaccg cccctgccc cagcgccac ctcctccccg      60 gccggcggcc gacggtggac gcggcggcga gccgcgggca ggagccggag cccgcgcccg   120
gaggcggggt ggaggggtc ggggctcgcg acgttgccct gaaactttc gtccaacttc     180 tgcgctgttc tcgttccgga ggagccgtgg tccgtgccgg gctgccgag ccgagtggca    240 ccgggagaag tgctcgctcg gccggggagg agccgcagtc ggaggagggg gaggaggaag   300
aagagaagga agaggagaag gggccgcggt ggcgactcgg ctctcggaag ccgggctcat   360
ggacgggtga ggcagctgtg tgcacagaca gtgctccagc cgcgcgcgcg ccccaggccc   420
tggcccgggc ctcggctccg agaggaagag gagcccgcct gggcgccgag gagagcgggc   480
cgccccgcag cccgagccgg agaggagcg cgagccgcgc cggccccggc caggcctccg   540
aaaccatgaa ctttctgctc tcttgggtac attggagcct tgccttgctg ctctaccttc   600
```

```
accatgccaa gtggtcccag gctgcaccca tggcagaagg agggcagaaa ccccacgaag    660
tggtgaagtt catggatgtc taccagcgca gcttctgccg tcccatcgag accctggtgg    720
acatcttcca ggagtaccca gatgagattg agttcatttt caagccgtcc tgtgtgcccc    780
tgatgcggtg cggggctgc tgtaatgacg aaagtctgga gtgtgtgccc actgaggagt    840
tcaacatcac catgcagatt atgcggatca aacctcacca aagccagcac ataggagaga    900
tgagcttcct acagcataac aaatgtgaat gcagaccaaa gaaagataaa gcaaggcaag    960
aaaatccctg tgggccttgc tcagagcgga gaaagcattt gtttgtacaa gatccgcaga   1020
cgtgtaaatg ttcctgcaaa aacacagact cgcgttgcaa ggcgaggcag cttgagttaa   1080
acgaacgtac ttgcagatgt gacaagccga ggcggtgagc cgggctggag gaaggagcct   1140
ccctcagggt ttcgggaacc agacgtctca ccaggaaaga ctgacacaga actacccata   1200
gccgccgcca ccaccaccac accaccacca ccaccatcga cagaacaatc ctgaatccag   1260
aaacctgaca tgaaggaaga ggaggctgtg cgcagagcac tttgggtccg gagcgtgagg   1320
ctccggcaga agcattcatg ggcgggtgac ccagcacggt tcctcttgga attggattgc   1380
cattttattt ctcttgctgc taaatcaccg agcccggaag attagagagt tttatttctg   1440
ggattcctgt agacacaccc acccacatac atacatacat ttatatatat atatatatta   1500
tatatataaa aataaatata tatattttat atatat                             1536

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaagcggct gtactgcaa                                                  19

<210> SEQ ID NO 8
<211> LENGTH: 2122
<212> TYPE: DNA
<213> ORGANISM: Bos taurus

<400> SEQUENCE: 8
ccggggccgc gccgcggagc gcgtcggagg ccggggccgg ggcgcggcgg ctccccgcgc     60
ggctccaggg gctcggggac cccgccaggg ccttggtggg gccatggccg ccgggagcat    120
caccacgctg ccagccctgc cggaggacgg cggcagcggc gctttcccgc cgggccactt    180
caaggacccc aagcggctgt actgcaagaa cgggggcttc ttcctgcgca tccaccccga    240
cggccgagtg gacggggtcc gcgagaagag cgacccacac atcaaactac aacttcaagc    300
agaagagaga ggggttgtgt ctatcaaagg agtgtgtgca aaccgttacc ttgctatgaa    360
agaagatgga agattactag cttctaaatg tgttacagac gagtgtttct tttttgaacg    420
attggagtct aataactaca atacttaccg gtcaaggaaa tactccagtt ggtatgtggc    480
actgaaacga actgggcagt ataaacttgg acccaaaaca ggacctgggc agaaagctat    540 acttttctt ccaatgtctg ctaagagctg atcttaatgg cagcatctga tctcatttta    600
catgaagagg tatatttcag aaatgtgtta atgaaaaag aaaatgtgt acagtgagct    660 gctcagtttg ggtaactgtt cagataaccg tttatctaag agtaaaatat ttaaccattg    720
ccttagtttt tttttaaaga aaaaacacaa taacagcaaa aattcctgga aaatgtatac    780
```

```
atttccactt tttatacagc atttcctttt atccagtgaa acttacttaa agctacaatc      840
tttcatacag tgtgcttcat ttgaagaggc ttttaaaatg tgtacaaaca agttttcttc      900
atggaaatta tagacattag aaaattaaag tcatatttag ttattacccc aaatgtccac      960
tactcctata atatggcaca cattaatcta catgtacaac ttacttaaac atgtacaact     1020
tacttaaaca ttttaaaaac atgtaaatat gaatttaatc cattcctgtc atagttttgt     1080
aattgtctgg cagtttcttg tgatagagtt tatagaacaa gcctgtgtaa actgctggca     1140
gttcttccat ggtcagatca attttgtcaa acccttcttt gtacccatac agcagcagcc     1200
ttgcaactct gcttgttatg ggagtcgtat ttttagtctt gactagatcg ctgagattca     1260
tccactcaca ctttaagcat tcacgctggc aaaaatttat ggtgaatgaa tatggcttta     1320
agcggcaaat aatatacata tctgacttcc caaaagctcc tggatgggtg tgctgttgcc     1380
gaatactcag gagggatctg aattcggatt ttataccagt ctcttcaaaa acttctcgaa     1440
ctgctgtatc tcctacataa aagaaaatgt acaaatcaat aacgattata cttttagaaa     1500
tttaatcaaa gattttcaga taaggaagca ttattatgta aagattcaaa aggtaaaaat     1560
ttaccctaag aaaagaaagc tttccctgta aactctgtcc tctggacatt ctgaaaaaac     1620
aaagtatttt cttaccactg tatagctaag aagcttttga ataatatttt ctttggcttc     1680
tacttgcaag cttacccatc tatatatatg tattttggga gtcacatatt tttaaattct     1740
tcctgcttta tttcccaaaa gttaatattc ctgtatattt tttcattatt atcttgttcc     1800
tgattatcca ttaaaactgc ctaaactgat aaacatttga agtaagaaaa agtgatccat     1860
tcttctttac aaaagtctgt agagctgcag aatatataga actaggaaat gattcaaatc     1920
atccctggtc tctcctggga ctgtcaggcc tctgaagtca taggtcggat ttcgttataa     1980
ccattttgtt atgctcttct agttattctg tcagtggaat cccaccatgg taatttctgg     2040
cattttcttt gtttcttgct gtttcaaaga acttggattc attcttctaa caccaaaatg     2100
ctacagtcat cagaagttta aa                                              2122

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctggacacc aactactgct tcag                                              24

<210> SEQ ID NO 10
<211> LENGTH: 1117
<212> TYPE: DNA
<213> ORGANISM: Bos taurus

<400> SEQUENCE: 10
aggccatact ggccctttac aacagtaccc gcgaccgggt ggccggggaa agtgccgaaa       60
cggagcctga gccagaggcg gactactacg ccaaggaggg cacccgcgtg ctaatggtgg      120
aatacggcaa caaatctat gacaaaatga agtctagctc gcacagcata tatatgttct      180
tcaacacgtc cgagctccgg gaagcggtgc ccgaacctgt gttgctctct cgggcagacg      240
tgcgcctgct gaggctcaag ttaaaagtgg agcagcacgt ggagctgtac cagaaatata      300
gcaacaattc ctggcgctac ctcagcaacc ggctgctcgc ccccagcgac tcaccggagt      360
ggctgtcctt tgacgtcact ggagttgtgc ggcagtggct gacccgcaga gaggaaatag      420
```

-continued

```
agggctttcg cctcagtgcc cactgttcct gtgacagtaa agataacacg cttcaagtgg    480
acattaacgg gttcagttcc ggccgccggg gtgacctcgc caccattcac ggcatgaacc    540
ggcccttcct gctcctcatg gccacccctc tggagagggc ccagcacctg cacagctccc    600
gccaccgccg agccctggac accaactact gcttcagctc cacagaaaag aactgctgtg    660
ttcgtcagct ctacattgac ttccggaagg acctgggctg gaagtggatt catgaaccca    720
aggggtacca cgccaatttc tgcctggggc cctgcccttg catctggagc ctggatacac    780
agtacagcaa ggtcctggcc ctgtacaacc agcacaaccc gggcgcttcg gcggcgccgt    840
gctgcgtgcc tcaggcgctg gagcccctgc ccatcgtgta ctacgtgggc cgcaagccca    900
aggtggagca gttgtccaac atgatcgtgc gctcctgcaa gtgcagctga ggccccgtcc    960 cacccaaca gcccccgccc cgtagcccg ccacccggca gccggcccc gccccgccc     1020 gcctcaccag gactgtattt aaggacacag caccaccccc cccccccac tcccatcaag    1080 cccacctggg gtccattaaa ggtggcgaga ggaaaaa                             1117
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctacatttg ttcgtgttgg a                                               21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgtttaactc aagctgcctc gcct                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatcagatgc tgccattaag atca                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgatcatgt tggacaactg ctcc                                            24